(12) United States Patent
Siegel

(10) Patent No.: US 10,105,221 B2
(45) Date of Patent: Oct. 23, 2018

(54) METHOD AND APPARATUS FOR PERCUTANEOUS DELIVERY AND DEPLOYMENT OF A CARDIOVASCULAR PROSTHESIS

(71) Applicant: CEDARS-SINAI MEDICAL CENTER, Los Angeles, CA (US)

(72) Inventor: Robert James Siegel, Beverly Hills, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 408 days.

(21) Appl. No.: 14/771,707

(22) PCT Filed: Mar. 6, 2014

(86) PCT No.: PCT/US2014/021410
§ 371 (c)(1),
(2) Date: Aug. 31, 2015

(87) PCT Pub. No.: WO2014/138482
PCT Pub. Date: Sep. 12, 2014

(65) Prior Publication Data
US 2016/0008129 A1  Jan. 14, 2016

Related U.S. Application Data

(60) Provisional application No. 61/774,463, filed on Mar. 7, 2013.

(51) Int. Cl.
*A61F 2/24* (2006.01)
*A61B 17/00* (2006.01)
(Continued)

(52) U.S. Cl.
CPC ...... *A61F 2/2427* (2013.01); *A61B 17/00234* (2013.01); *A61B 17/1227* (2013.01);
(Continued)

(58) Field of Classification Search
CPC ............ A61F 2/2427; A61B 17/00234; A61B 17/1227; A61B 17/1285; A61B 2017/00243
See application file for complete search history.

(56) References Cited

U.S. PATENT DOCUMENTS

| 4,777,951 A | 10/1988 | Cribier et al. |
|---|---|---|
| 5,201,880 A | 4/1993 | Wright et al. |

(Continued)

FOREIGN PATENT DOCUMENTS

| EP | 1 674 040 | 6/2006 |
|---|---|---|
| EP | 1 539 015 | 4/2011 |

(Continued)

OTHER PUBLICATIONS

Bhargava et al., "Biosense Left Ventricular Electromechanical Mapping", Asian Cardiovasc Thorac Ann 1999, 7:345-52.
(Continued)

*Primary Examiner* — Julie A Szpira
(74) *Attorney, Agent, or Firm* — Knobbe Martens Olson & Bear LLP

(57) ABSTRACT

Catheter apparatuses and methods are provided for repairing heart valves, particularly mitral valves. The method includes providing a catheter having an elongate, flexible body, with a proximal end and a distal end. The distal end can be transluminally advanced from the left atrium through the mitral valve and along the left ventricular outflow tract into the ascending aorta. A valve repair device is deployed to permanently connect leaflets at a mid-section of a mitral valve while permitting medial and lateral portions of the natural leaflets to open and close. The valve repair device detachably connects the distal and proximal ends of the catheter.

20 Claims, 23 Drawing Sheets

(51) Int. Cl.
  *A61B 17/122* (2006.01)
  *A61B 17/128* (2006.01)
(52) U.S. Cl.
  CPC ............ *A61B 17/1285* (2013.01); *A61B 2017/00243* (2013.01); *A61B 2017/00292* (2013.01); *A61B 2017/00353* (2013.01); *A61B 2017/00473* (2013.01)

(56) References Cited

U.S. PATENT DOCUMENTS

| | | | |
|---|---|---|---|
| 5,573,540 A | 11/1996 | Yoon | |
| 5,575,799 A | 11/1996 | Bolanos et al. | |
| 5,609,598 A | 3/1997 | Laufer et al. | |
| 5,626,588 A | 5/1997 | Sauer et al. | |
| 5,716,367 A | 2/1998 | Koike et al. | |
| 6,029,671 A | 2/2000 | Stevens et al. | |
| 6,051,014 A | 4/2000 | Jang | |
| 6,090,096 A | 7/2000 | St. Goar et al. | |
| 6,117,144 A | 9/2000 | Nobles et al. | |
| 6,117,145 A | 9/2000 | Wood et al. | |
| 6,136,010 A | 10/2000 | Modesitt et al. | |
| 6,165,183 A | 12/2000 | Kuehn et al. | |
| 6,197,043 B1 | 3/2001 | Davidson | |
| 6,206,893 B1 | 3/2001 | Klein et al. | |
| 6,269,819 B1 | 8/2001 | Oz et al. | |
| 6,287,321 B1 | 9/2001 | Jang | |
| 6,312,446 B1 | 11/2001 | Huebsch et al. | |
| 6,312,447 B1 | 11/2001 | Grimes | |
| 6,325,067 B1 | 12/2001 | Sterman et al. | |
| 6,328,757 B1 | 12/2001 | Matheny | |
| 6,461,366 B1 | 10/2002 | Seguin | |
| 6,575,971 B2 | 6/2003 | Hauck et al. | |
| 6,629,534 B1 | 10/2003 | St. Goar et al. | |
| 6,635,068 B1 | 10/2003 | Dubrul et al. | |
| 6,752,813 B2 | 6/2004 | Goldfarb et al. | |
| 6,770,083 B2 | 8/2004 | Seguin | |
| 6,926,715 B1 | 8/2005 | Hauck et al. | |
| 6,932,792 B1 | 8/2005 | St. Goar et al. | |
| 6,945,978 B1 | 9/2005 | Hyde | |
| 7,048,754 B2 | 5/2006 | Martin et al. | |
| 7,226,467 B2 | 6/2007 | Lucatero et al. | |
| 7,563,267 B2 | 7/2009 | Goldfarb et al. | |
| 7,569,062 B1 | 8/2009 | Kuehn et al. | |
| 7,604,646 B2 | 10/2009 | Goldfarb et al. | |
| 7,632,308 B2 | 12/2009 | Loulmet | |
| 7,635,329 B2 | 12/2009 | Goldfarb et al. | |
| 7,666,204 B2 | 2/2010 | Thornton et al. | |
| 7,704,269 B2 | 4/2010 | St. Goar et al. | |
| 7,736,388 B2 | 6/2010 | Goldfarb et al. | |
| 7,811,296 B2 | 10/2010 | Goldfarb et al. | |
| 7,828,819 B2 | 11/2010 | Webler et al. | |
| 7,854,762 B2 | 12/2010 | Speziali et al. | |
| 7,938,827 B2 | 5/2011 | Hauck et al. | |
| 7,981,123 B2 | 7/2011 | Seguin | |
| 8,123,703 B2 | 2/2012 | Martin et al. | |
| 8,172,856 B2 | 5/2012 | Eigler et al. | |
| 8,216,256 B2 | 7/2012 | Raschdorf, Jr. et al. | |
| 8,216,302 B2 | 7/2012 | Wilson et al. | |
| 8,303,608 B2 | 11/2012 | Goldfarb et al. | |
| 8,323,334 B2 | 12/2012 | Deem et al. | |
| 8,409,273 B2 | 4/2013 | Thornton et al. | |
| 8,545,551 B2 | 10/2013 | Loulmet | |
| 8,568,472 B2 | 10/2013 | Marchand et al. | |
| 8,992,605 B2 | 3/2015 | Zakai et al. | |
| 9,023,099 B2 | 5/2015 | Duffy et al. | |
| 9,060,858 B2 | 6/2015 | Thornton et al. | |
| 9,474,605 B2 | 10/2016 | Rowe et al. | |
| 9,498,330 B2 | 11/2016 | Solem | |
| 9,763,658 B2 | 9/2017 | Eigler et al. | |
| 2001/0005787 A1 | 6/2001 | Oz et al. | |
| 2002/0013571 A1 | 1/2002 | Goldfarb et al. | |
| 2003/0120340 A1 | 6/2003 | Liska et al. | |
| 2004/0044350 A1 | 3/2004 | Martin et al. | |
| 2004/0260322 A1 | 12/2004 | Rudko et al. | |
| 2005/0033446 A1 | 2/2005 | Deem et al. | |
| 2005/0107871 A1 | 5/2005 | Realyvasquez et al. | |
| 2005/0143811 A1 | 6/2005 | Realyvasquez | |
| 2005/0222489 A1 | 10/2005 | Rahdert et al. | |
| 2006/0229708 A1 | 10/2006 | Powell et al. | |
| 2006/0293739 A1 | 12/2006 | Vijay | |
| 2007/0032850 A1* | 2/2007 | Ruiz | A61F 2/2412 623/1.11 |
| 2007/0038293 A1 | 2/2007 | St.Goar et al. | |
| 2007/0055303 A1 | 3/2007 | Vidlund et al. | |
| 2007/0270943 A1 | 11/2007 | Solem et al. | |
| 2009/0048668 A1 | 2/2009 | Wilson et al. | |
| 2009/0177266 A1 | 7/2009 | Powell et al. | |
| 2010/0217283 A1 | 8/2010 | St.Goar et al. | |
| 2010/0298929 A1 | 11/2010 | Thornton et al. | |
| 2011/0029071 A1 | 2/2011 | Zlotnick et al. | |
| 2011/0066233 A1 | 3/2011 | Thornton et al. | |
| 2011/0106245 A1 | 5/2011 | Miller et al. | |
| 2011/0218620 A1 | 9/2011 | Meiri et al. | |
| 2011/0224655 A1 | 9/2011 | Asirvatham et al. | |
| 2011/0264208 A1 | 10/2011 | Duffy et al. | |
| 2011/0319989 A1 | 12/2011 | Lane et al. | |
| 2012/0010700 A1 | 1/2012 | Spenser | |
| 2012/0065464 A1* | 3/2012 | Ellis | A61B 17/0644 600/104 |
| 2012/0078360 A1 | 3/2012 | Rafiee | |
| 2012/0095547 A1 | 4/2012 | Chuter | |
| 2012/0116418 A1 | 5/2012 | Belson et al. | |
| 2012/0191181 A1 | 7/2012 | Kassab et al. | |
| 2012/0245678 A1 | 9/2012 | Solem | |
| 2012/0310331 A1* | 12/2012 | Eigler | A61B 17/0469 623/2.11 |
| 2012/0310334 A1 | 12/2012 | Dolan | |
| 2013/0018414 A1 | 1/2013 | Widimski et al. | |
| 2013/0030522 A1 | 1/2013 | Rowe et al. | |
| 2013/0253547 A1 | 9/2013 | Goldfarb et al. | |
| 2014/0039607 A1 | 2/2014 | Kovach | |
| 2014/0058502 A1 | 2/2014 | Marchand et al. | |
| 2014/0236198 A1 | 8/2014 | Goldfarb et al. | |
| 2016/0000562 A1 | 1/2016 | Siegel | |
| 2017/0143478 A1 | 5/2017 | Schwartz et al. | |
| 2017/0245988 A1 | 8/2017 | Siegel et al. | |
| 2017/0325842 A1 | 11/2017 | Siegel et al. | |

FOREIGN PATENT DOCUMENTS

| | | |
|---|---|---|
| WO | WO 00/60995 | 10/2000 |
| WO | WO 01/26557 | 4/2001 |
| WO | WO 03/049619 | 6/2003 |
| WO | WO 2004/012583 | 2/2004 |
| WO | WO 2014/138284 | 9/2014 |
| WO | WO 2016/040526 | 3/2016 |
| WO | WO 2016/077783 | 5/2016 |
| WO | WO 2017/015632 | 1/2017 |

OTHER PUBLICATIONS

Black MD, M., Divisiona of Pediatric Cardiac Surgery, Standford University School of Medicine, California, USA, Minimally Invasive Pediatric Cardiac Surgery, Online Article in 4 pages.
Ethicon Wound Closure Manual—Chapter 6, Research and Development at Ethicon, Inc.—An Ongoing Process of Change and Improvement, Online at www.ethiconinc.com in 4 pages.
Gersak MD, Ph.D., B., "Mitral Valve Repair or Replacement on the Beating Heart", The Heart Surgery Forum #2000-1989, Jun. 8, 2000, pp. 232-237, 2000 Forum Multimedia Publishing, LLC.
Perclose A-T, 6F Suture-Mediated Closure (SMC) System, Instructions for Use disctributed in the U.S. by Abbott laboratories, Inc. 2002, 2006 Abbott Laboratories in 11 pages.
Quealy et al., "Use of Combined Intravascular Ultrasound and PTCA Catheter: Clinical Utility", Chapter 12, pp. 245-250.
International Search Report and Written Opinion issued in PCT Application No. PCT/US2014/021410, dated Jun. 25, 2014, in 15 pages.

(56) References Cited

OTHER PUBLICATIONS

International Preliminary Report on Patentability issued in PCT Application No. PCT/US2014/021410, dated Sep. 8, 2015, in 8 pages.

* cited by examiner

METHOD AND APPARATUS FOR PERCUTANEOUS DELIVERY AND DEPLOYMENT OF A CARDIOVASCULAR PROSTHESIS

BACKGROUND OF THE INVENTION

Field of the Invention

This application is directed to cardiac valve prostheses and to apparatuses and methods for deploying such devices in a minimally invasive manner.

Description of the Related Art

A major type of heart disease is valvular insufficiency, also called valvular regurgitation, which is characterized by the improper closing of a heart valve. A heart valve consists of a number of leaflets—either two or three—that swing open to allow blood to flow forward (anterograde) out of a heart chamber, and then swing closed to form a tight seal, preventing blood from leaking backwards (retrograde). Valvular insufficiency may result from a variety of problems with the components which make up the valve—for example, the leaflets themselves may degenerate, the tissue cords which tether the leaflets to muscles within the heart may break, or the ring of tissue within which the valve is seated (called the "annulus") may expand after heart attacks or from congestive heart failure. Each of these problems leads to a common element in valvular regurgitation: when closed, the edges of the valve leaflets no longer fit snuggly next to each other and allow retrograde flow.

Mitral regurgitation (MR) (insufficiency of the valve which connects the left atrium with the left ventricle of the heart) and tricuspid regurgitation (TR) (insufficiency of the valve which connects the right atrium with the right ventricle of the heart) contribute significantly to cardiovascular morbidity and mortality. MR is a debilitating disease that can lead to serious complications and possible death. Its symptoms include shortness of breath, rapid respirations, palpitations, chest pain, and coughing. MR leads to heart failure and pulmonary edema and also predisposes patients to other conditions, such as stroke, arterial embolus, and arrhythmias, including atrial fibrillation and lethal ventricular arrhythmias. Detection and timely effective treatment of MR leads to higher survival rates, decreased complications, and increased comfort for patients.

Currently, the only commercially available method of definitively repairing atrioventricular valvular regurgitation is open-heart surgery. In this procedure, the patient is first anesthetized and then subject to a thoracotomy. Access to the patient's heart is achieved by making a large incision, retracting the skin, muscle, and bony structures. The surgeon must stop the beating of the heart and cut it open to directly visualize the valve. The surgeon then may repair the valve surgically, or remove the valve and implant a prosthetic valve. This requires placing the patient on cardiopulmonary bypass, which involves applying a heart-lung machine to the patient that circulates oxygenated blood throughout the body in place of the working heart and lungs. After the heart is bypassed and is stopped, its structure can be visualized.

Although open-heart surgery is a successful method of repairing or replacing faulty heart valves, it poses a significant risk to the wellbeing of the patient, including death, severe injury, and disability. There is a risk of ischemic or other damage to the heart and other vital organs resulting from the discontinuance of the heart's normal function. The heart-lung machine may also cause abnormalities of the patient's circulatory, respiratory, hematologic and neurologic systems. There is a risk of stroke and other consequences from emboli released into the blood during the surgery and during initiation of cardiopulmonary bypass. There is a risk of heart attack. Significant damage occurs to the tissues and bone retracted from the patient's chest while gaining access to the heart. Post-operative complications such as wound infection, pneumonia, and venous thrombosis occur because of the extent of incisions and the patient's debilitated state. Also, cardiopulmonary bypass carries with it a risk of renal insufficiency, particularly in patients with borderline kidney function. Such patients may require dialysis after surgery due to the stress on the kidneys during bypass. Consequently, a patient's recovery can be painful, discomforting, long in duration, and costly.

A minimally invasive, beating-heart procedure that would not expose the patient to these risks is therefore desirable. Moreover, a limited surgical approach or percutaneous approach would decrease or eliminate the tissue trauma that occurs from the extensive incisions of open-heart surgery, sparing patients pain, improving recovery time, and decreasing post-operative complications.

A very large population exists that would benefit from an alternative method of valve repair. Approximately 10% of coronary artery bypass surgeries include mitral valve repair or replacement, which amounts to 75,000 to 100,000 of such procedures per year world-wide. In addition, significant MR and/or TR complicate 30-60% of patients with congestive heart failure, contributing to their impaired cardiac function and causing significant morbidity. However, because of the significant risks involved in open-heart surgery, many of the patients are unable to undergo valve repair. Thus, a successful percutaneous or minimally-invasive method of valve repair on the beating heart would have extraordinary clinical benefit.

No commercial products have been marketed that successfully repair the mitral valve of the human heart with a minimally invasive, beating-heart procedure. Several factors are responsible for this. First, the heart and its associated valves are not directly visualized or accessible. One can use imaging techniques such as fluoroscopy or echocardiography, but these provide a two-dimensional image and a limited field of view. Three-dimensional imaging technologies, including advanced forms of echocardiography, are available but only in a limited number of medical centers and only to very few clinicians trained to use them. Second, it is extremely difficult to immobilize the rapidly moving heart valve leaflets for repair purposes while the heart is beating. Not only are the leaflets moving back and forth rapidly, but also they each have a different shape and geometry. Thus, no single device or methodology has successfully been used to repair heart valves in a minimally invasive manner on a beating heart.

Efforts have been made to commercialize catheter based valve clip devices, though such devices are not yet approved for use in the United States. These devices are delivered by a catheter system percutaneously on a catheter device that is articulated to steer a clip device into place. The catheter system is placed over a guidewire. The device has a dilator that facilitates insertion into the left atrium. Thereafter, the dilator is removed and the clip is advanced at the distal end of an inner portion of the catheter system through an outer portion of the catheter system into the left atrium. The inner portion is adjusted to orient the clip such that the clip points down toward the left ventricle. Once pointed downward, arms of the clip are opened. An innermost portion of the catheter system is then projected from the left atrium into the left ventricle, below the valve leaflets. Thereafter, the clip is retracted and closed to hold the leaflets together to reduce MR.

Although these clip devices can be explained relatively simply, the actual use is not simple. For example, steering and orienting the clip is a delicate operation that requires skill foreign to most cardiologists. The delivery device is relatively large at 24 French. It is heavy and rigid and more analogous to a robotic arm than to generally much more flexible devices regularly used by cardiologists. Because of its rigidity, it is steered using dials that actuate a complex mechanism to orient it in three degrees of freedom. This intricate control system for orienting the rigid arm is only accurately positioned through the use of complex imaging technologies. The rigidity of the system eliminates tactile feedback to the doctor and thus imaging is the only means for achieving and/or confirming placement.

While technically able to repair a mitral valve through peripheral access, these devices and the procedures in which they are used still are very costly to the patient and to the health care system in general. While these clips devices are described as being able to release, re-approach, and recapture the leaflets, such re-working procedures increase the overall procedure time which is disadvantageous for the patient and the physician. For example, the MitraClip procedure is indicated as taking 2 to 4 hours, which is comparable to open heart valve repair surgery. In practice, the procedure can take two to three times longer than this due to poor initial placement, release and re-grasping efforts. Also, the patient must be under general anesthesia, and both an interventional cardiologist and an echo cardiologist must be present during the procedure. These and other aspects of the MitraClip design discussed in the EU Heart Journal article of May 23, 2011 make it inconvenient and costly to use.

SUMMARY OF THE INVENTION

Disclosed herein is a method of performing a procedure in the heart. In the method, a catheter is provided that has an elongate flexible body, a proximal end, and a distal end. The catheter also has a procedure zone spaced proximally apart from the distal end. The proximal and distal ends are separable from the procedure zone. The catheter is advanced antegrade through the mitral valve and through the aortic valve and into the aorta. When so advanced, the procedure zone is positioned upstream from the aortic valve. A procedure is performed from the procedure zone. At least one of the proximal portion and the distal portion are separated from the procedure zone. The proximal and distal portions of the catheter are separately removed from the patient.

In another embodiment, a method of orienting a first and second tissue grasper with respect to the mitral valve is provided. The method includes providing a catheter having an elongate, flexible body, with a proximal end, a distal end and first and second tissue graspers spaced apart from the distal end. The distal end of the catheter is transluminally advanced from the left atrium through the mitral valve and along the left ventricular outflow tract into the ascending aorta. Such advancement positions the first and second tissue graspers adjacent a central zone of the mitral valve. Thereafter, the distal end of the catheter is drawn out of a peripheral artery.

In another embodiment, a method of repairing a mitral valve is provided. The method includes providing a catheter having an elongate, flexible body, with a proximal end and a distal end. The distal end is transluminally advanced from the left atrium through the mitral valve and along the left ventricular outflow tract into the ascending aorta. A valve repair device is deployed to permanently connect leaflets at a mid-section of a mitral valve while permitting medial and lateral portions of the natural leaflets to open and close. The valve repair device detachably connects the distal and proximal ends of the catheter.

In another embodiment, a system is provided for performing a procedure in the heart. The system includes a catheter having an elongate flexible body, a proximal end, a distal end, and a procedure zone. The procedure zone is spaced proximally apart from the distal end. Proximal and distal portion of the catheter are separable from the procedure zone. In certain embodiments, the catheter is advanceable antegrade through the mitral valve. That is, the elongate body can have a length to extend from a peripheral venous site to the heart, into the atria of the heart, and through the mitral valve. The elongate body further can have a length to extend from a peripheral venous site through the heart and aortic valve and into the aorta. The elongate body further can have a length to extend from a peripheral venous site through the heart such that the procedure zone is positioned upstream from the aortic valve. The procedure zone can be configured to perform a procedure in the heart. The proximal portion can be separable from the distal portion from, at or adjacent to the procedure zone. The elongate of the catheter can be configured such that a distal portion of the catheter can extend to a peripheral arterial site, e.g., when the proximal portion is disposed form the heart to a peripheral venous site. The distal portion is configured to be separated from the procedure zone by actuating the distal portion at the arterial site such that the distal portion can be removed from the arterial site while the proximal portion can be removed from the peripheral venous site.

In another embodiment, a system is provided for orienting first and second tissue graspers of a heart prosthesis with respect to the mitral valve. The system includes a catheter having an elongate, flexible body, with a proximal end and a distal end. First and second tissue graspers are provided in the system spaced apart from the distal end of the elongate flexible body. The catheter is configured to be advanceable from a peripheral venous site to the left atrium and through the mitral valve and into the ascending aorta (e.g., along the left ventricular outflow tract). The catheter is configured to position the first and second tissue graspers adjacent to a central zone of the mitral valve. A distal portion of the catheter is configured to be disposed in a peripheral artery and through a percutaneous access site while the graspers are adjacent to the central zone such that a distal portion of the catheter can be drawn out of the peripheral artery.

In another embodiment, a mitral valve repair apparatus is provided that includes a catheter having an elongate, flexible body. The body can have a proximal end and a distal end. A distal portion, e.g., the distal end, of the body is advanceable from the left atrium through the mitral valve and along the left ventricular outflow tract into the ascending aorta. The elongate, flexible body can be configured to reach the heart from a femoral venous or other peripheral venous site. The apparatus also includes a valve repair device configured to permanently connect leaflets at a mid-section of a mitral valve while permitting medial and lateral portions of the natural leaflets to open and close. The valve repair device is detachably coupled with the distal and proximal ends of the catheter.

Various embodiments are also directed to a mitral valve prosthesis. The prosthesis includes an elongate arcuate body, a based, and arcuate anterior and posterior leaflet grasping elements. The elongate arcuate body has a proximal end and a distal end. The base is disposed between the proximal and distal ends of the elongate body. The arcuate anterior leaflet grasping element is articulated at or adjacent to the distal end of the elongate body. The arcuate anterior leaflet grasping element is movable between an open position and a closed position. The arcuate posterior leaflet grasping element is articulated at or adjacent to the distal end of the elongate body. The arcuate posterior leaflet grasping element is movable between an open position and a closed position.

In certain embodiments of the mitral valve prosthesis, when the posterior leaflet grasping element is in the closed position, the posterior leaflet grasping element is received in a space at least partially bounded by the base.

In certain embodiments of the mitral valve prosthesis, a flush surface is provided between the base and side surfaces of at least one of the anterior and poster leaflet grasping elements.

In certain embodiments of the mitral valve prosthesis, a lumen and a fluid actuator (e.g., hydraulic, pneumatic, etc.) are disposed in the base for actuating at least one of the anterior and poster leaflet grasping elements.

In certain embodiments of the mitral valve prosthesis, a first lumen and a first fluid actuator is disposed in the base for actuating the anterior leaflet grasping element and a second lumen and a second fluid actuator is disposed in the base for actuating the posterior leaflet grasping element.

In certain embodiments of the mitral valve prosthesis, an indexing feature is disposed on a proximal portion of the prosthesis for providing a selected rotational position of the prosthesis relative to a catheter body.

In certain embodiments of the mitral valve prosthesis, a control member channel is disposed on a proximal face of the base for engaging a guide wire or push element.

In certain embodiments of the mitral valve prosthesis, a retention member is provided that is configured to be advanced over a side surface of the arcuate body to a position around at least one of the anterior and posterior leaflet grasping elements to hold the grasping element against the base.

In certain embodiments of the mitral valve prosthesis, a bight is formed or provided between the base and at least one the anterior and posterior grasping elements, e.g., when one or both of the anterior and posterior leaflet grasping element is in the open position. The bight is proximally facing, e.g., when having a larger transverse dimension adjacent to the proximal end of the prosthesis than adjacent to the distal end thereof.

In certain embodiments of the mitral valve prosthesis, a hinge is provided between at least one of [a] the base and a distal portion of the anterior leaflet grasping element and [b] the base and a distal portion of the posterior leaflet grasping element.

In certain embodiments of the mitral valve prosthesis, a spring is coupled with a first portion of the posterior leaflet grasping element and an actuator coupled with a second portion of the posterior leaflet grasping element, the hinge being disposed between the first and second portions.

DETAILED DESCRIPTION OF THE PREFERRED EMBODIMENT

Figure 1:
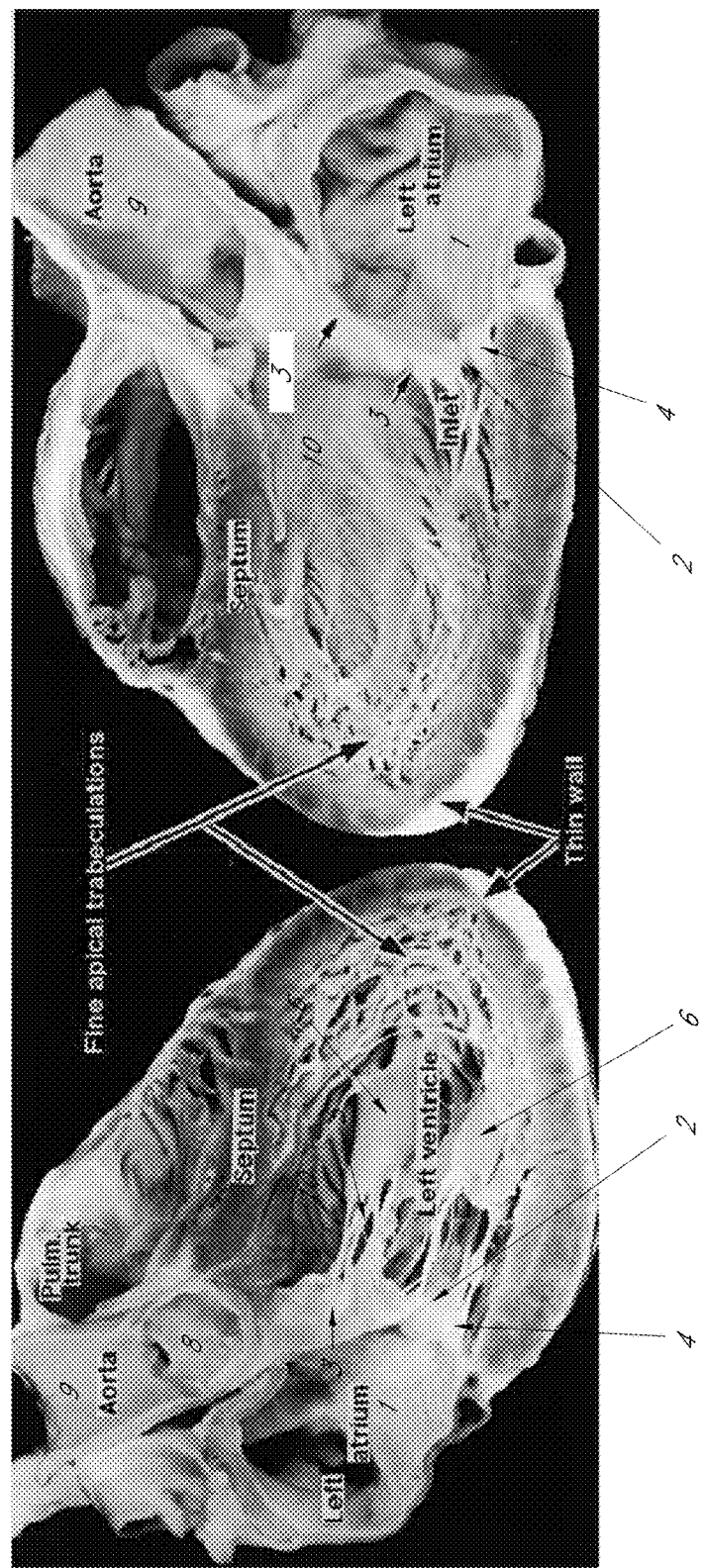
FIG. 1 is a photograph of a pathologic specimen of a human heart sectioned along its long axis, demonstrating the pertinent anatomical structures and landmarks important to device operation.

In FIG. 1, a longitudinal section of the human heart is shown demonstrating the left atrium 1, the mitral valve orifice 2, the anterior leaflet 3 of the mitral valve, and the posterior leaflet 4 of the mitral valve. The subvalvular apparatus consists of the numerous chordae tendinae 5 and the papillary muscles 6. The left ventricular outflow tract (LVOT) 10 is a channel formed by the anterior leaflet 3 of the mitral valve and the interventricular septum.

Figure 2:
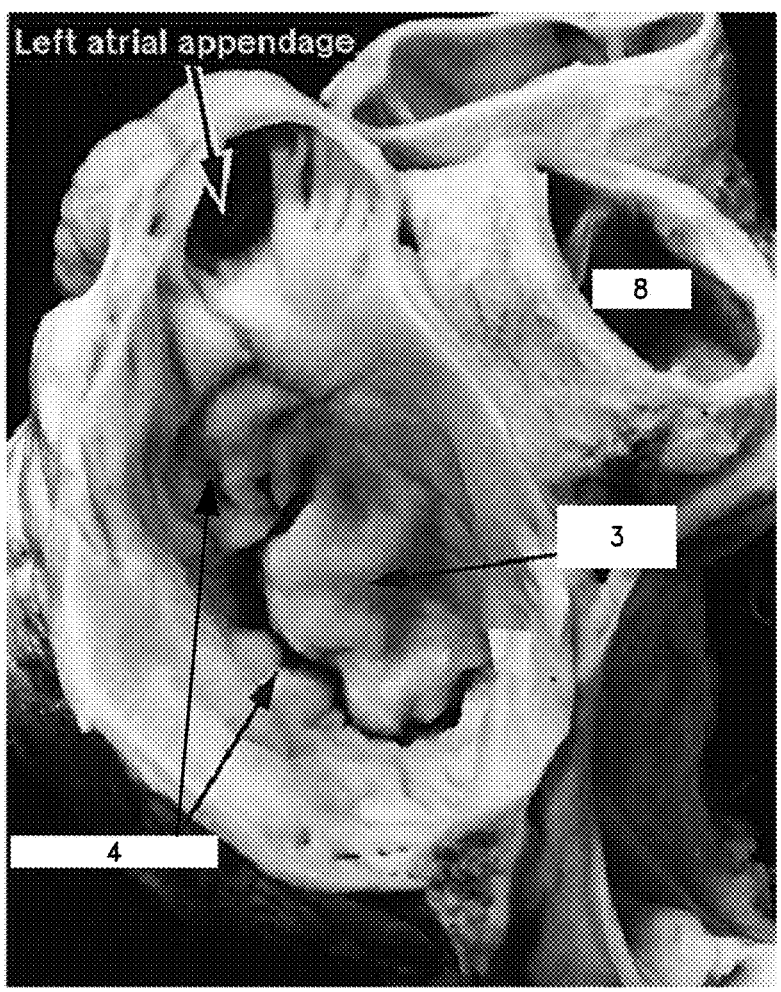
FIG. 2 is a photograph of a pathologic specimen of a human heart, sectioned in short axis at the level of the left atrium, demonstrating the anatomy of the mitral valve leaflets as viewed from the perspective of the left atrium and the approach according to certain embodiments of the invention.
Figure 2A:
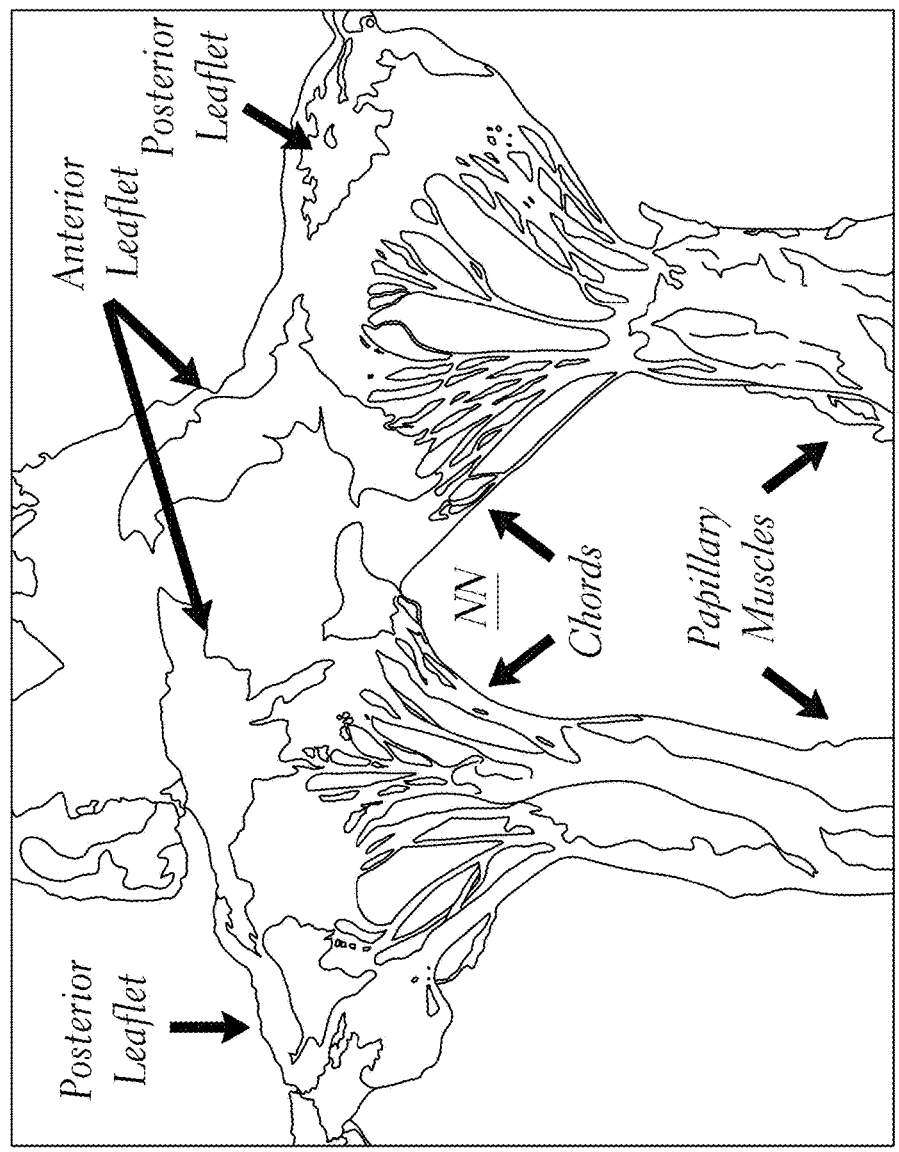
FIG. 2A is a photograph of a partial dissection of a mitral valve showing the sub-valvular apparatus in greater detail.

In FIG. 2, a short axis view of the mitral valve is seen at the level of the left atrium. This demonstrates the asymmetric nature of the mitral valve leaflets. The posterior leaflet 4 has a broad base and of narrow width, while the anterior leaflet 3 has a relatively narrow base and a substantial width. FIG. 2A is a partial dissection of the mitral valve further illustrating the sub-valvular apparatus. These figures illustrate the trajectory along which a catheter device is advanced according to this disclosure to position a valve repair device. As discussed in greater detail below, the trajectory is from the left atrium 1, through the mitral valve orifice 2, between the papillary muscles 6, through the LVOT 10, across the aortic valve 8 and into the ascending aorta 9.

With particular reference to FIG. 2A, when properly positioned, the path will be centered between the posterior-most chord of the anterior portion of the sub-valvular apparatus and the anterior-most chord of the posterior portion of the sub-valvular apparatus. The superior aspects of these chordae extend toward one another, forming an anatomical narrows that is exploited by the methods and apparatuses herein for rapid positioning of a valve repair device. As discussed in greater detail below a trajectory extending from a wall of the aorta, through this narrows region and up through the mitral valve into the left atrium will roughly bisect the mitral valve in the medial-lateral direction. Thus, the methods and devices herein are less dependent upon difficult to interpret imaging technologies and the need to position and reposition a valve repair device to get a good result, e.g., significantly reducing MR.

I. Orienting a Valve Repair Device

FIGS. 3-9 illustrate methods for deploying a valve repair device. In these techniques, the valve repair device is a durable device and can be an apposing element, a fastening device, or a fastener that reduces MR. The valve repair device preferably is deployed to secure together a medial-lateral central zone of the valve to create a double orifice at the mitral valve. The valve repair device is configured to minimize a chance of leaflet tear, such as by grasping a sufficient area of the valve to reduce concentration of force, as discussed further below. FIGS. 16-20 illustrate an embodiment of a valve repair device that enhances coaptation compared to other mitral valve prostheses as discussed below and a system and method for deploying the valve repair device.

Figure 3:
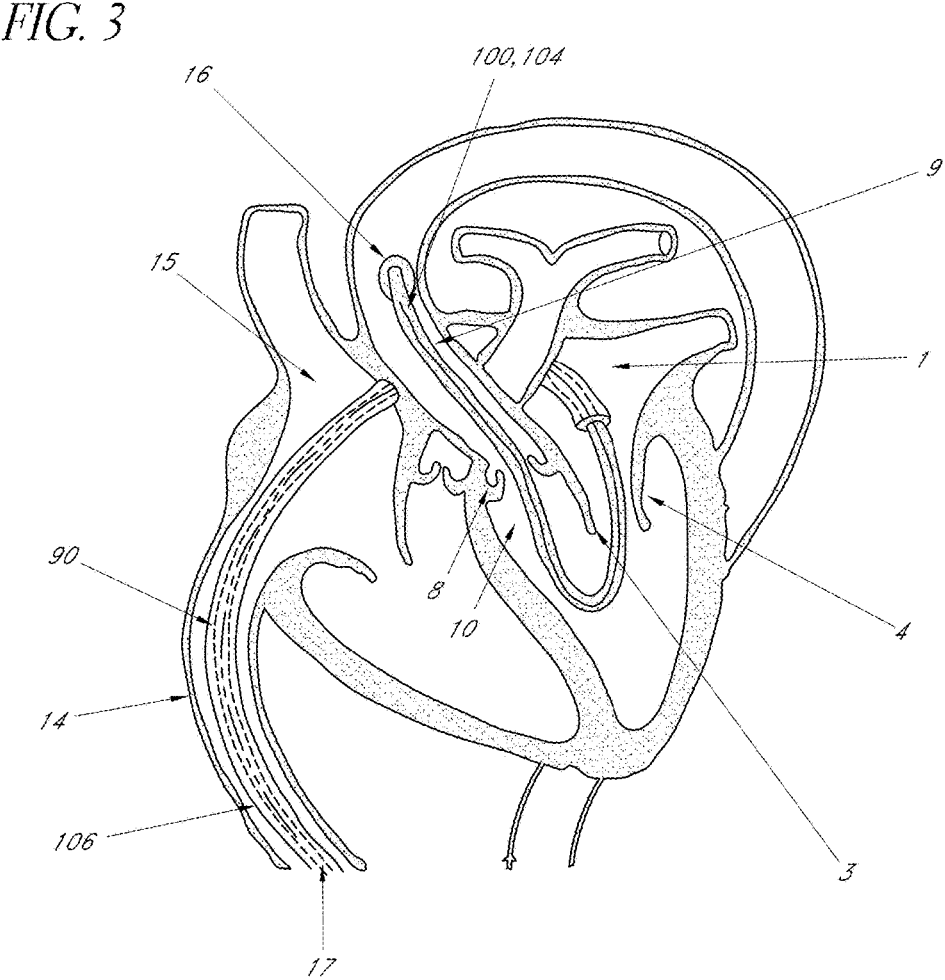
FIG. 3 is a schematic representation of a human heart and one embodiment of the present invention showing the position within the heart and blood vessels that provides correct orientation, the proximal end being accessible at a first peripheral venous location.

FIG. 3 shows the body of a catheter 100 with a distal portion 104 disposed in the heart and the ascending portion of the aorta 9. A method for delivering the catheter 100 to this position can include accessing a peripheral vein and providing access to the left atrium 1 through the atrial septum, e.g., by opening and/or enlarging the fossa ovalis. Standard transseptal access devices can be advanced into a femoral vein and through the inferior vena cava 14 to cross the atrial septum. In one embodiment a sheath 90 is advanced across the septum and into the left atrium. After access is provided, the catheter 100 can be advanced into the left atrium 1 and through the mitral valve between the anterior and posterior leaflets 3, 4. The catheter 100 can be further advanced into the LVOT 10 and into the aorta 9 in the position shown in FIG. 3. A proximal portion 106 of the catheter 100 extends proximally from the heart, e.g., through the sheath 90, and exits the body at a peripheral venous location, such as a femoral vein.

Figure 4:
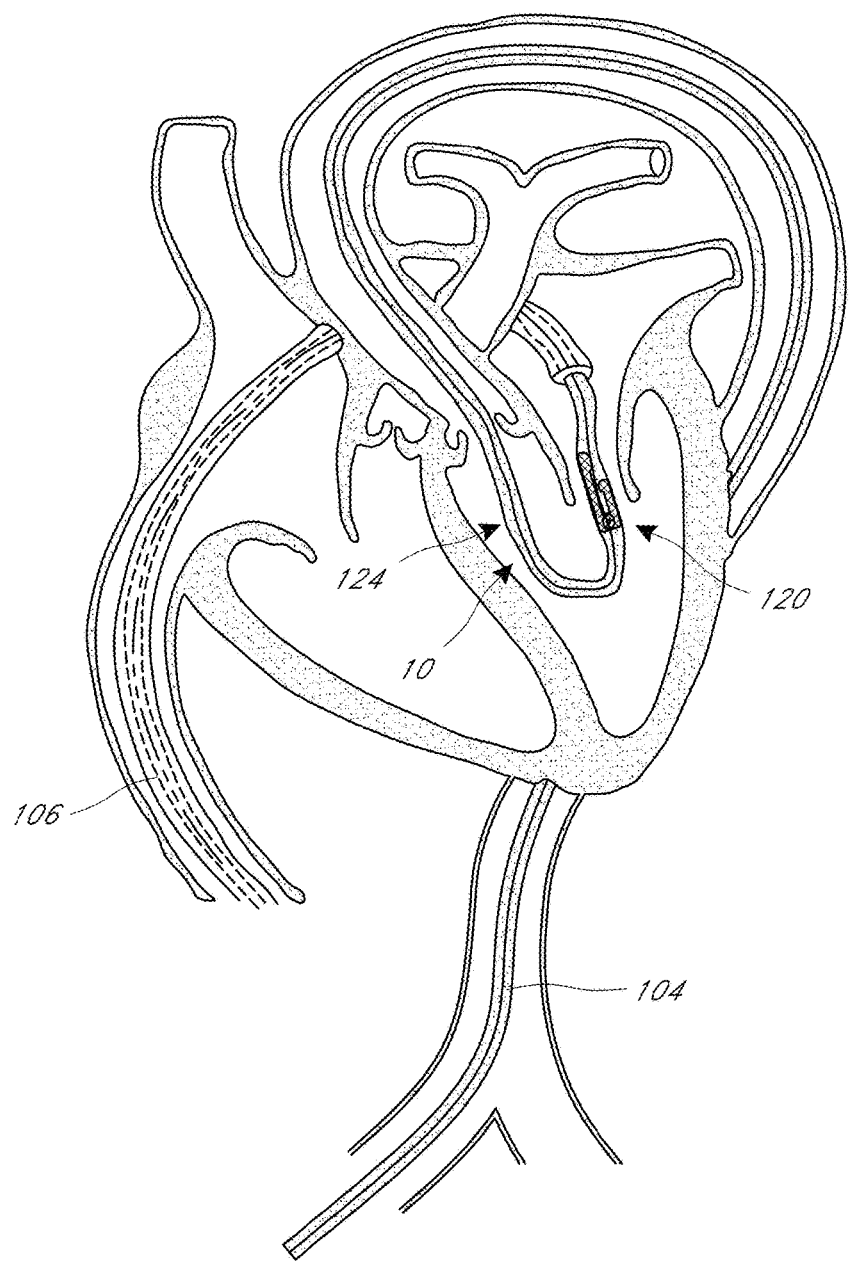
FIG. 4 is a schematic representation of a human heart and one embodiment of the present invention showing a distal portion of a catheter device advanced toward a femoral artery for accessing the distal portion.
Figure 10:
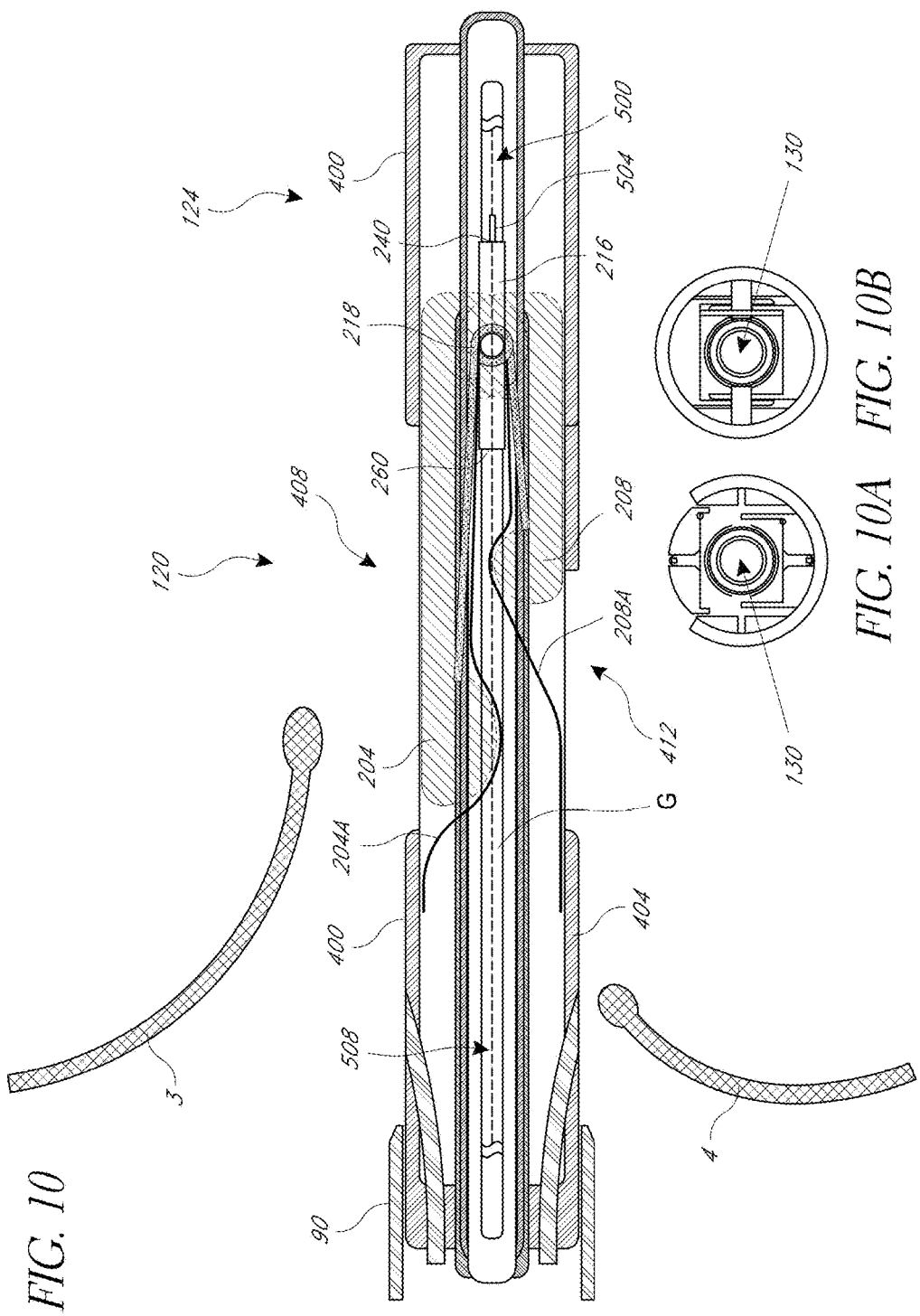
FIGS. 10-15 illustrate aspects of valve repair devices with pairs of arms configured to capture valve leaflets and their deployment at a valve.

FIG. 4 shows a later step in which the distal portion 104 of the catheter 100 is advanced over the arch of the aorta 9 and further toward a peripheral artery. FIG. 10 shows that a lumen 130 can be provided in the catheter 100. The lumen 130 can be sized to receive a guidewire for positioning the catheter 100. In some embodiments as discussed below, the lumen 130 can be used to deploy and operate an imaging device at least in an area within or adjacent to the heart, e.g., in a procedure zone. Advancing the catheter 100 in this manner can be accomplished by any standard technique, such as tracking a previously placed guidewire or a flow directed catheter. Access can be provided to the peripheral arterial site by conventional means. A snare or other grasping device can be used to draw the distal end of a guidewire or other tracking device out of the patient such that a continuous guiding track or circuit from peripheral venous access to peripheral arterial access is provided. The peripheral femoral venous access is a first access site and the femoral (or other peripheral) arterial access is a second access site, and the first and second access sites can be accessed simultaneous as discussed below.

In another embodiment, guiding devices such as guide wires are not used to deliver the distal portion 104 to the peripheral arterial site from the heart. Instead, the catheter 100 is directed unguided or retracted toward the vicinity of the second access site without a guidewire. A balloon or highly flexible distal region can be a useful structure for unguided delivery to a peripheral arterial site. A snare may then be used to capture the distal end of the distal portion 104. Either tracking a guiding device or by use of the snare, the distal end of the distal portion 104 of the catheter 100 can be directed or drawn out of the body at the peripheral arterial access site.

Figure 3A:
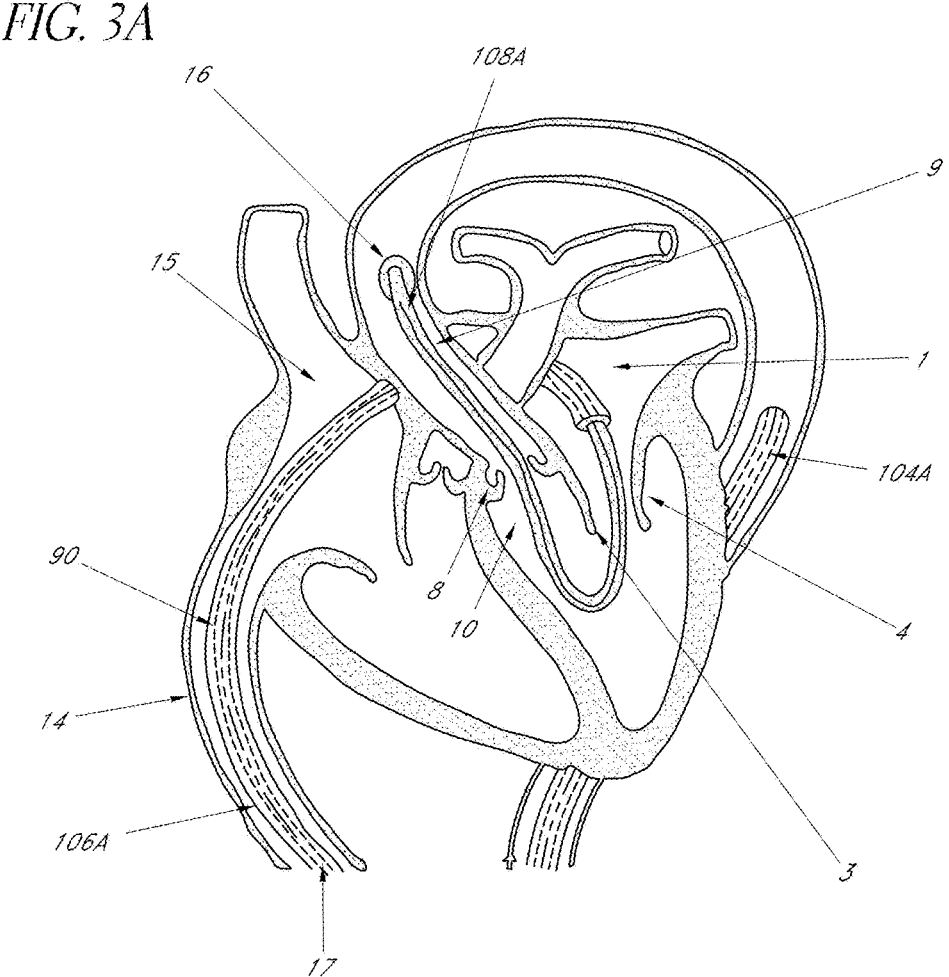
FIG. 3A illustrates part of a venous-arterial rail method that can be combined with the methods and apparatuses disclosed herein

FIG. 3A shows an alternative approach in which a distal end 108A of the proximal portion 106A can be position through the venous vasculature, across the mitral and aortic valves into the ascending aorta. A capture device 104A can be advanced from an arterial access site up the aorta and into vicinity of the distal end 108A of the proximal portion 106A. The capture device 104A can include a snare or other device to grasp the distal end 108A. In certain embodiments, the capturing device 104A is low profile such that it can engage the distal end 108A and form an outer surface that permits advancement of catheter bodies against flow from the arterial access site to the heart over the capture device 104A. This variation is discussed more in connection with FIG. 20.

Figure 4A:
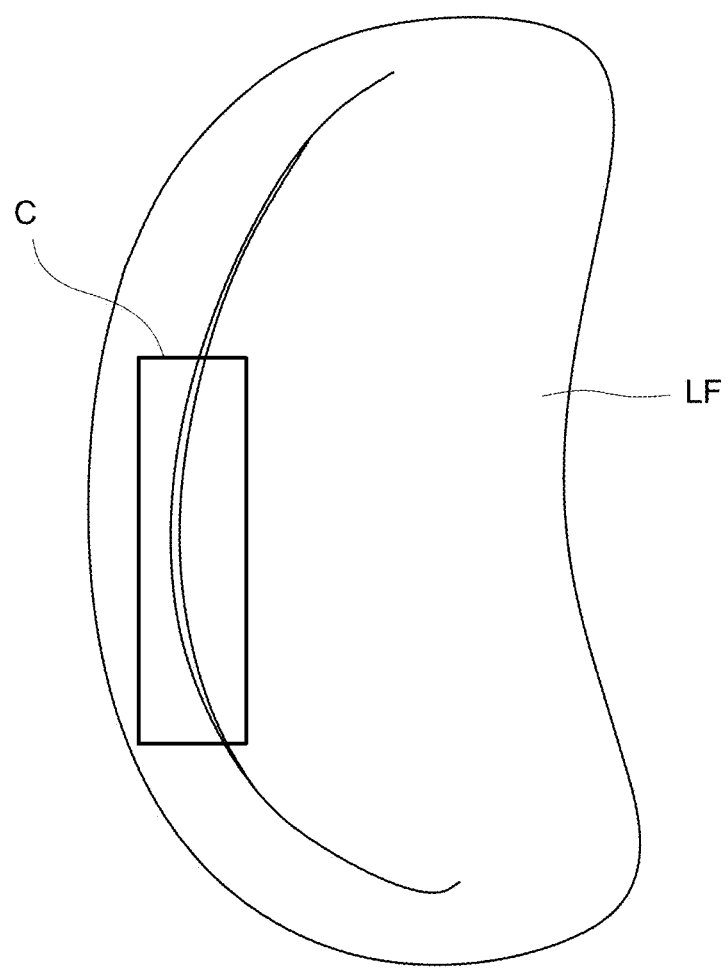
FIG. 4A is a schematic of a mitral valve showing placement of a procedure zone of a catheter device by interaction of an anchor zone with adjacent anatomy.

FIGS. 4 and 10 show that the catheter 100 has a procedure zone 120 and an anchor zone 124. The procedure zone 120 includes one or more devices for interacting with the vessel or a heart valve and/or deploying a valve repair device. The anchor zone 124 is configured to provide fast, consistent and accurate placement of the procedure zone 120 at the correct location along the valve. The positioning is better understood with reference to FIGS. 2A and 4A. As noted above in connection with FIG. 2A, an opening is defined in the sub-valvular apparatus between anterior papillary muscles and posterior papillary leading toward the LVOT 10. The distal portion 104 and anchor zone 120 passes through this opening as the catheter 100 is advanced to the position of FIG. 4. The anchor zone 124 is configured to engage the anatomy distal the mitral valve and to define a predictable, appropriate trajectory through the intervening anatomy and within the mitral valve. As the catheter 100 is placed, the procedure zone 120 follows a trajectory that intersects roughly the medial-lateral central zone of the mitral valve. In FIG. 4A, a box is drawn over a location of the zone C where the procedure zone 120 crosses the mitral valve when the anchor zone 124 engages distal anatomy and the proximal portion 106 of the catheter 100 is disposed proximally through the atrial septum. Because the procedures zone 120 naturally comes to rest at this location, subsequent manipulation is relatively minimal. This permits relatively simple manipulations to orient the procedure zone 120.

Further, to an extent interaction of the catheter 100 with central chordae tendinae can provide a guiding function to proper pre-positioning of the catheter 100. FIG. 2A shows that the posterior most of the chordae tendinae extending from the anterior papillary muscle and the anterior most of the chordae tendinae extending from the posterior papillary muscle further define the opening from the mitral valve to the LVOT 10 and to the aorta. A notch or narrows NN is defined where these chordae tendinae connect to the valve apparatus. When placed as in FIG. 4, the body of the catheter 100 comes to rest in this notch NN and as a result is in or very close to the zone C illustrated in FIG. 4A. Once advanced through the valve and into an anchoring connection with the anatomy, the proximal portion 106 of the catheter 100 can be subjected to a clockwise or counter-clockwise torque to orient the catheter body about its axis but still generally at the zone of coaptation of the leaflets. In other embodiments, a steerable wire can be used to allow anteflection, retroflection or other useful positioning maneuvers of the procedure zone 120. While the catheter 100 generally will place the procedure zone 120 in the area C illustrated in FIG. 4A, these subtle movements can optimize placement within that are, for example centering the procedure zone there.

This anchoring capability of the distal portion 104 of the catheter 100 provides for quicker and more efficient patient care. Other systems dispose a valve clip at the distal-most end of the delivery system and that rely on substantially free hand or proximal end only positioning of the valve in three dimensional space to approach the leaflets in reliance on sophisticated imaging. Although many procedures benefit from sophisticated imaging, and more maneuverability can be useful, free-hand or proximal end only placement of a clip requires too much manipulation to be conveniently and efficiently performed. Greater maneuverability carries with it the substantial chance of misplacement. Therefore, such devices are greatly complicated with features that enable the device to be un-clipped and re-clipped multiple times.

FIGS. 5-9 illustrate the ease of delivery of a valve repair device 200 using the catheter 100 placed as discussed above. The device 200 is advanced through the mitral valve between the leaflets 3, 4 into the left ventricle as the distal portion 104 of the catheter 100 is advanced through the second access site. In one embodiment, the valve repair device 200 is on, is part of, or comprises the procedure zone 120. In this context "valve repair device" is a broad term that includes any device or technique by which MR is reduced while still using the native valve leaflets to provide a valve function, including where the valve function is converted from a single orifice to a double orifice. This term also includes the mitral repair device of FIGS. 16-19 discussed in greater detail below. In one approach, the valve repair device 200 has an anterior element 204 and a posterior element 208. The anterior and posterior elements 204, 208 are configured to engage and secure the anterior and posterior leaflets 3, 4 respectively. Preferably the anterior and posterior elements 204, 208 are adapted to gather portions of the anterior and posterior leaflets 3, 4 and secure them against or within another portion of the valve repair device 200. Examples of structures that can be incorporated into the anterior and posterior elements 204, 208 are discussed in U.S. Pat. No. 6,752,813 to Goldfarb et al.; U.S. Pat. No. 7,635,329; and U.S. Pat. No. 7,604,646, all which is hereby incorporated by reference herein for this and any other purpose.

Figure 5:
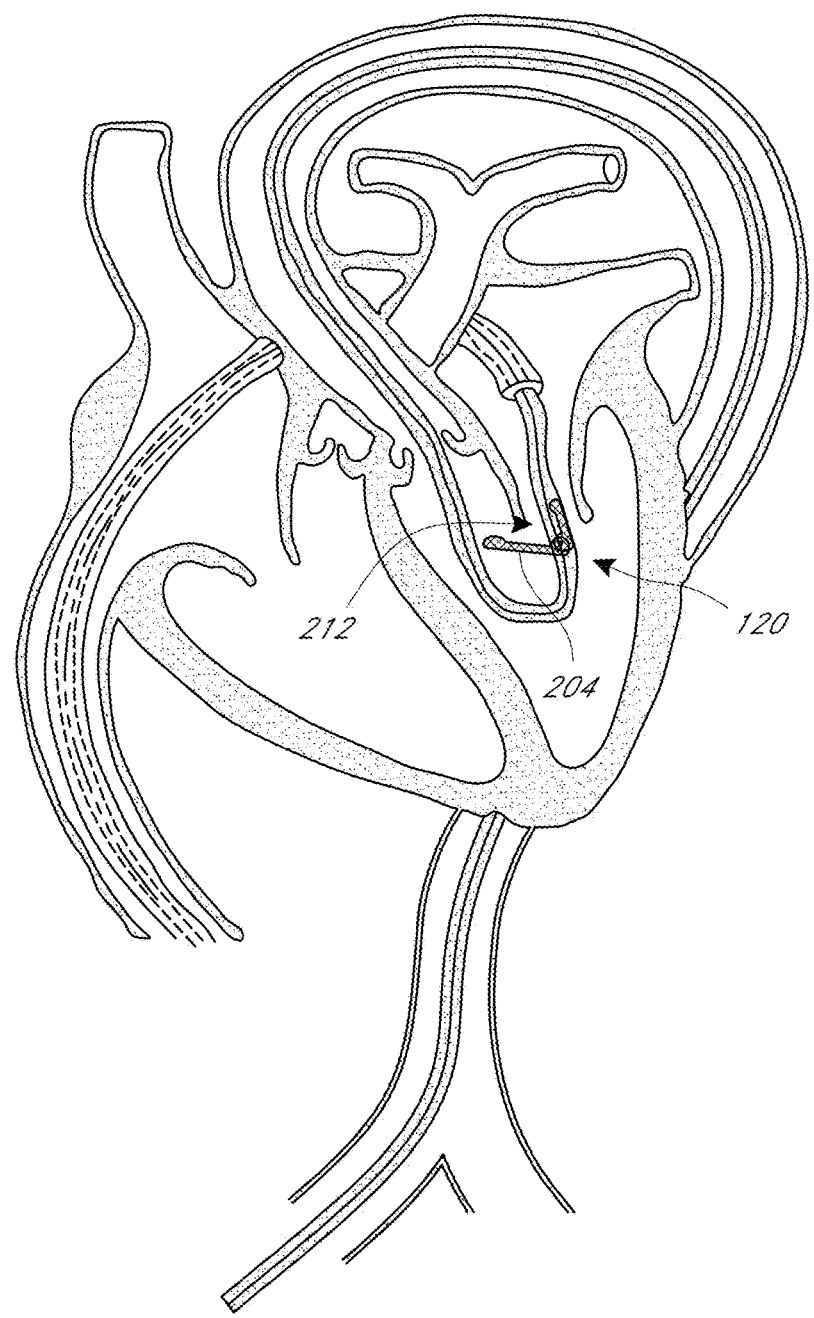
FIG. 5 is an image similar to that of FIG. 4, showing deployment of a valve treatment device.
Figure 6:
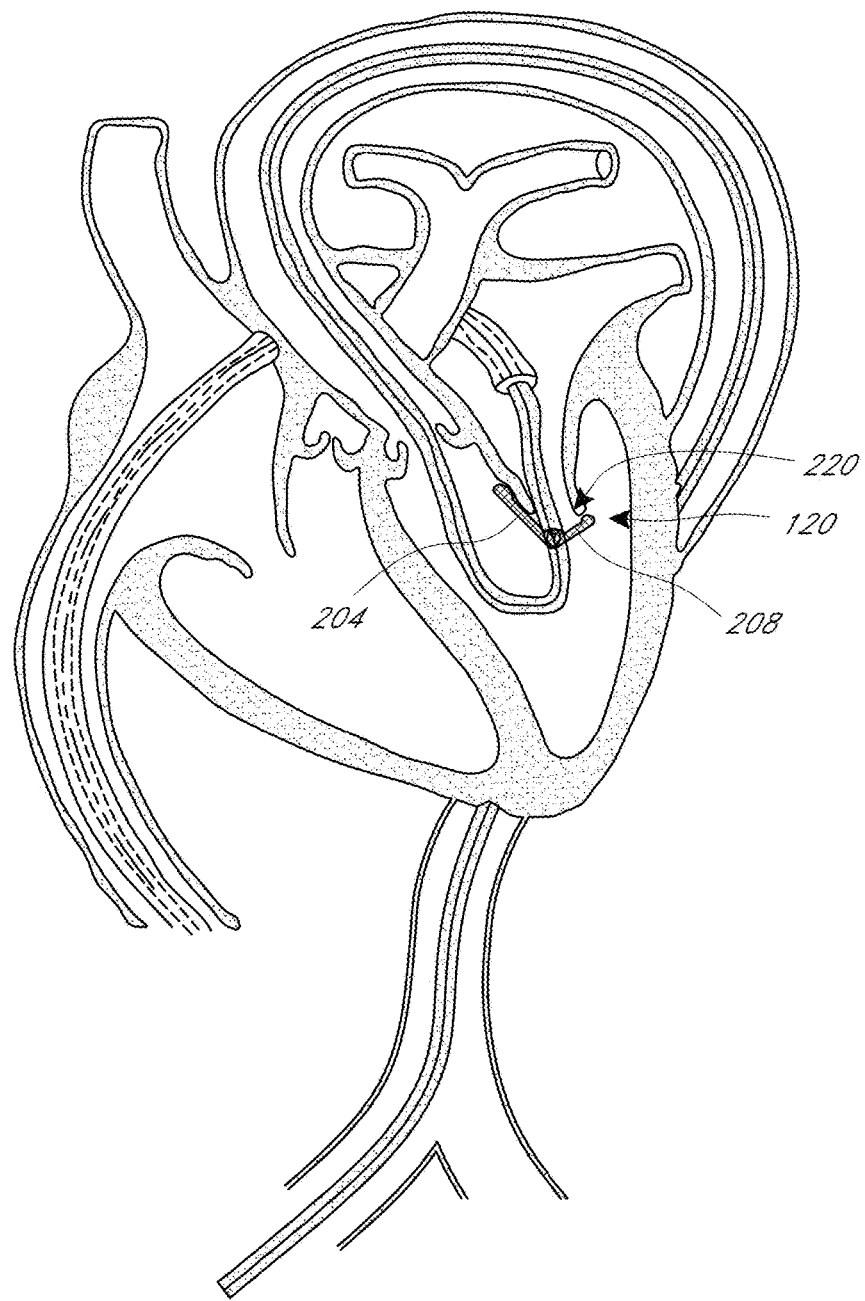
FIG. 6 is an image similar to that of FIG. 4, showing further deployment of a valve treatment device.
Figure 11:
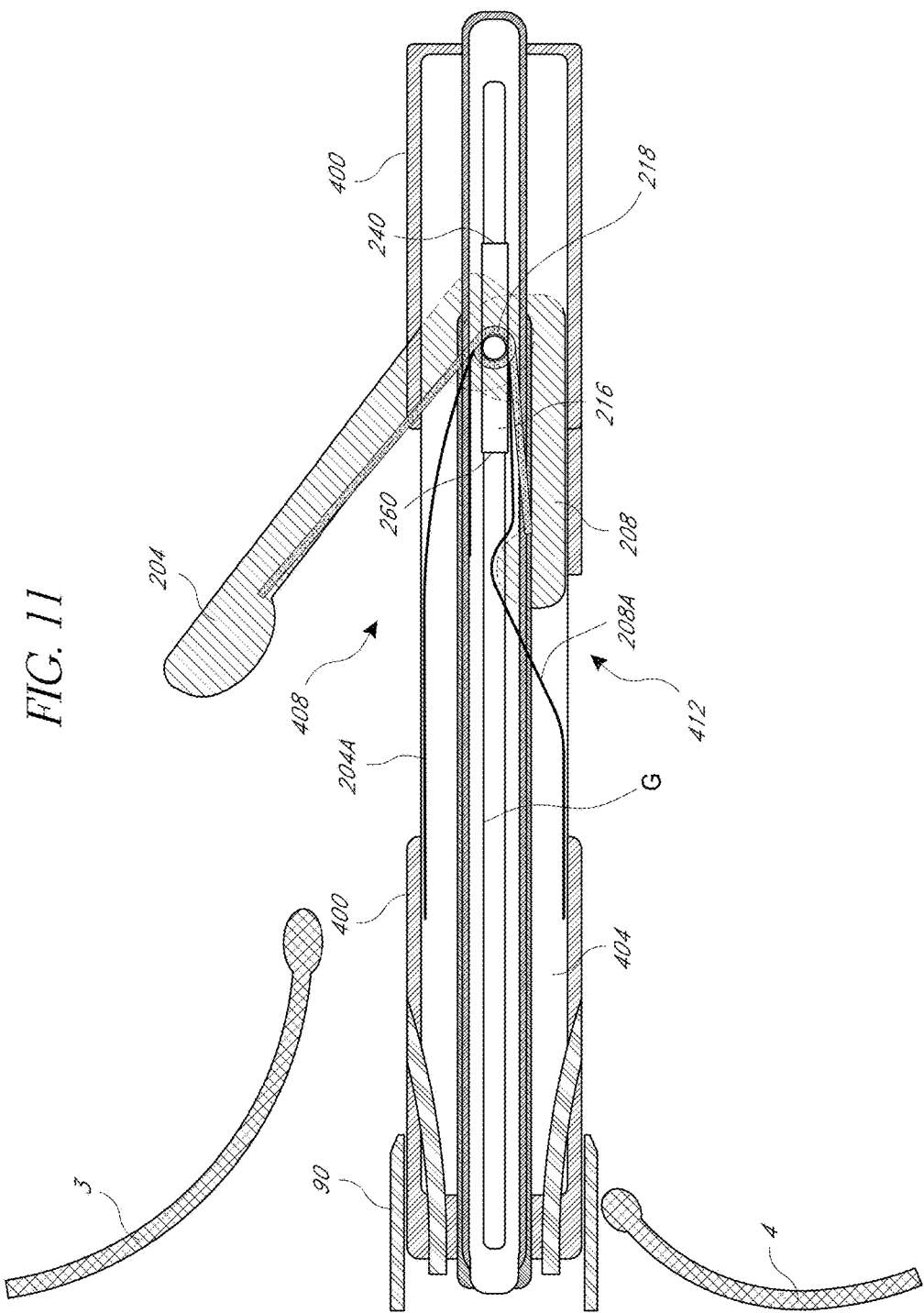

FIGS. 5 and 6 show one technique for capturing the leaflets. As discussed above, this procedure generally is to be performed on a beating heart, in which the mitral valve leaflets 3, 4 are moving rapidly relative to the procedure zone 120. FIGS. 5 and 11 show that the anterior element 204 can be deployed to create a proximally oriented channel or bight 212 between the element 204 and a central hub 216 of the device 200 that is suitable for receiving the valve therein. After the anterior element 204 is deployed slight proximal movement of the catheter 100 causes the leaflet 3 to be disposed in the bight 212. Although the valve is still moving as the heart beats, the anterior leaflet 3 is disposed in or through the bight 212 and remains temporarily gathered. In other words, although the mitral valve is operating and the anterior element 204 is open, the leaflet 3 remains in the bight 212.

Figure 13:
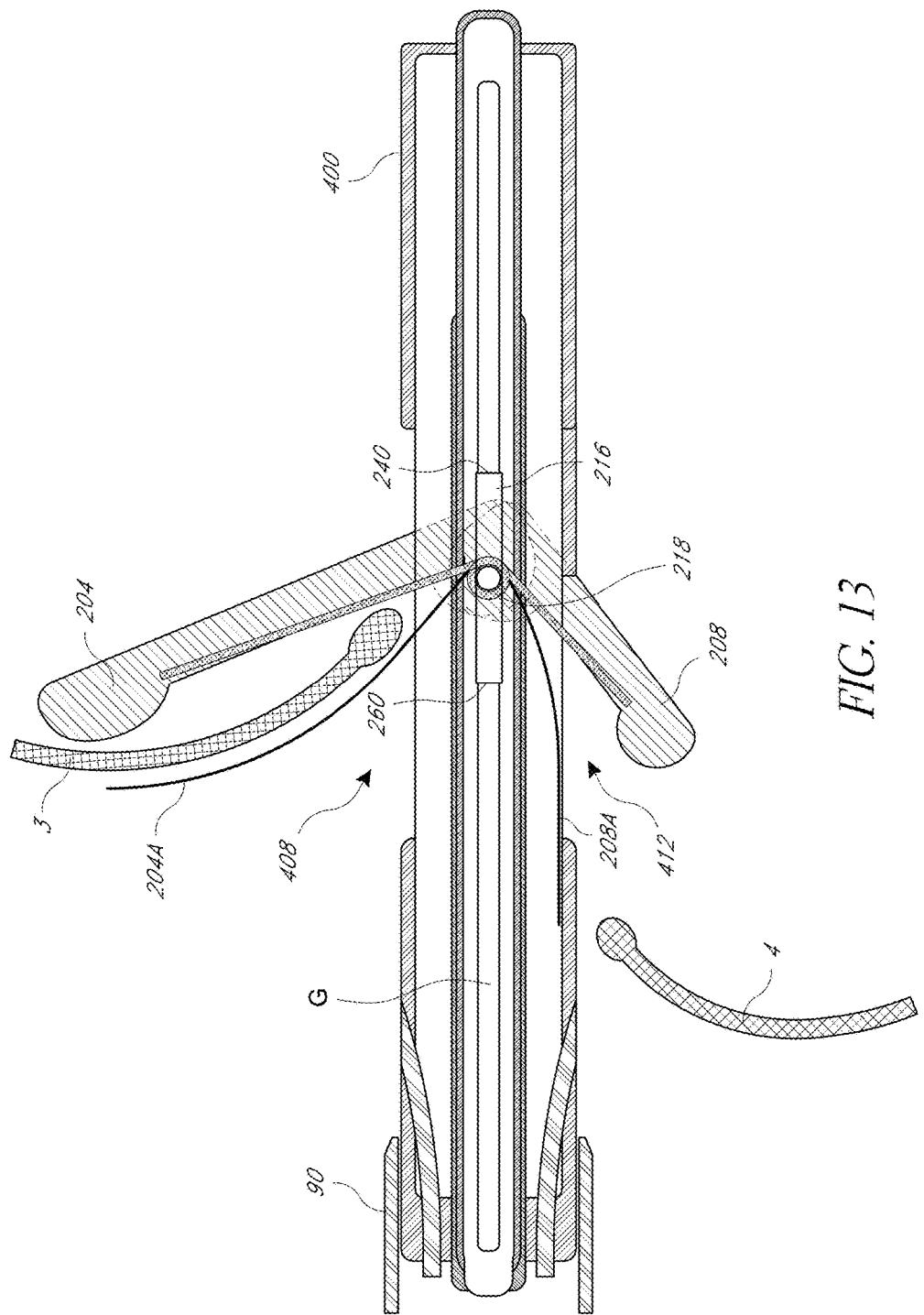

Thereafter, the posterior element 208 is deployed exposing a bight 220 between the element 208 and the hub 216. FIGS. 5 and 13 show the bight 220 in more detail. Slight proximal movement of the catheter 100 causes the leaflet 4 to be disposed in the bight 220. In certain embodiments, suction or a grasper device can be deployed from the catheter to maintain the leaflet in the bight 212, 220, as discussed in U.S. Pat. No. 7,635,329, which is incorporated by reference herein in its entirety and for this purpose. The Appendix includes this patent as part of this application.

The slight proximal movement to position the leaflets 3, 4 in the bights 212, 220 may be preceded with some manipulation of the catheter 100. The manipulation will cause the anterior and posterior elements 204, 206 to be deployed. For example, as discussed in connection with FIGS. 10-14 below the catheter 100 can have a plurality of windows that perm it egress of the anterior and posterior elements 204, 208 for capturing the leaflets 3, 4 respectively. In some cases, a torque applied to the proximal portion 106 can cause the anterior and posterior elements 204, 206 to pivot to the orient the bights 212, 220 on the ventricular side of the mitral valve zone C. As discussed above, the natural position of the catheter body 100 should align the procedure zone 120 substantially equally spaced from medial and lateral edges of the mitral valve opening. Thus the clinician can focus efforts on angular orientation of the anterior and posterior elements 204, 208, which orientation can be achieved with as few as one degree of freedom of movement.

Figure 7:
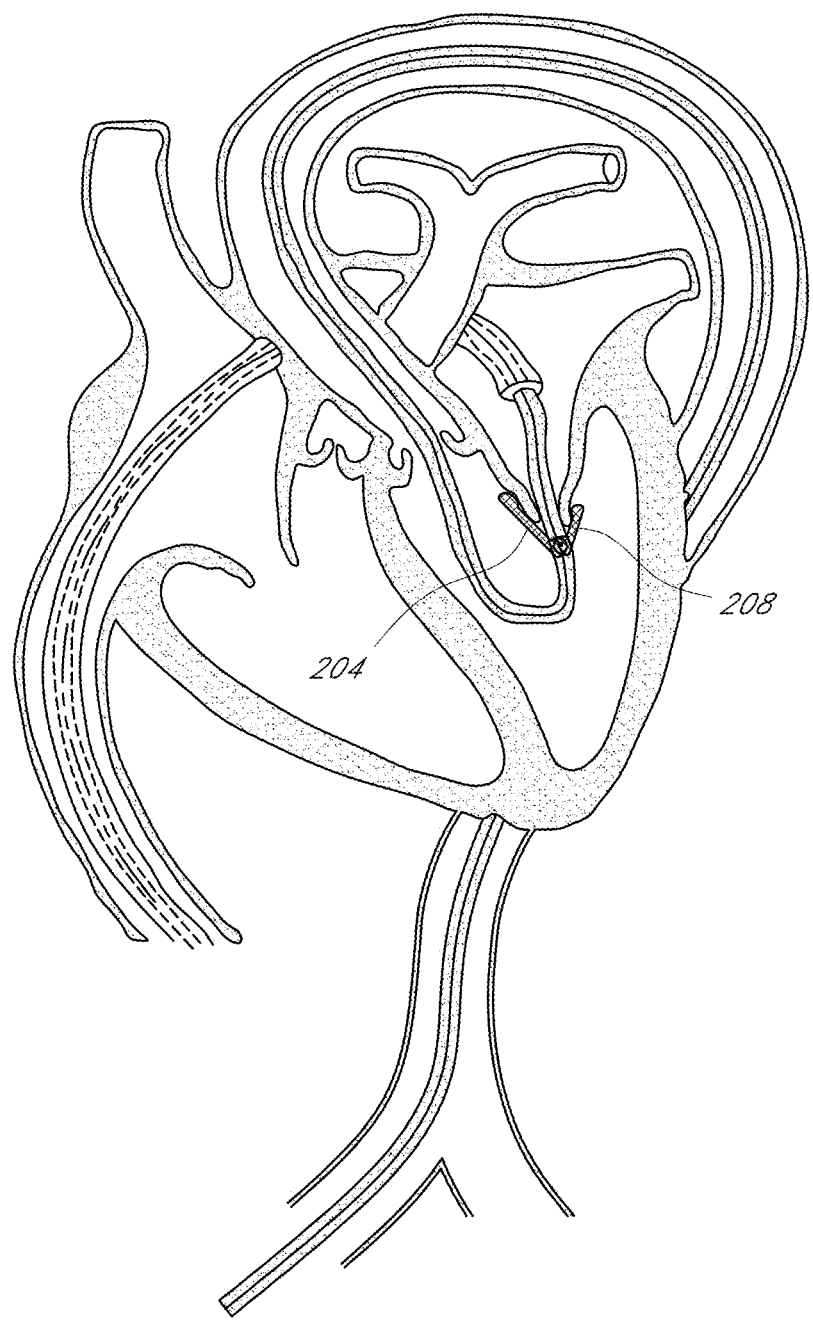
FIG. 7 is an image similar to that of FIG. 4, showing full engagement of a valve treatment device.

FIG. 7 illustrates a technique in which both leaflets 3, 4 are captured by the valve repair device 200. As discussed in connection with the incorporated matter, the device 200 captures the leaflets 3, 4 by actuating the elements 204, 208 toward the hub 216 to close the bights 212, 220. Various closure mechanisms can be used. For example, a spring hinge 218 can be disposed between the hub 216 and one or both of the anterior and posterior elements 204, 208. The spring can be store strain energy in the open state, e.g., when bights 212, 220 are enlarged and in a free state when the bights 212, 220 are closed. Alternatively, wire-actuated mechanisms can be disposed in the valve repair device 200 and/or the catheter 100 to pull the anterior and posterior elements 204, 208 against the hub 216 to close the bights 212, 220. As discussed below, the closure of the bights 212, 220 occurs sequentially, e.g., anterior bight 212 first and posterior bight 220 second. An advantageous design would involve closing the anterior bight 212 first because the anterior leaflet 3 is generally harder to catch. The range of motion of the anterior leaflet is greater and has a larger excursion, and thus is harder to catch. In some embodiments, as discussed in connection with FIGS. 10-14 below, the leaflets are captured between atrial and ventricular structures of the heart in a sandwich fashion.

Figure 8:
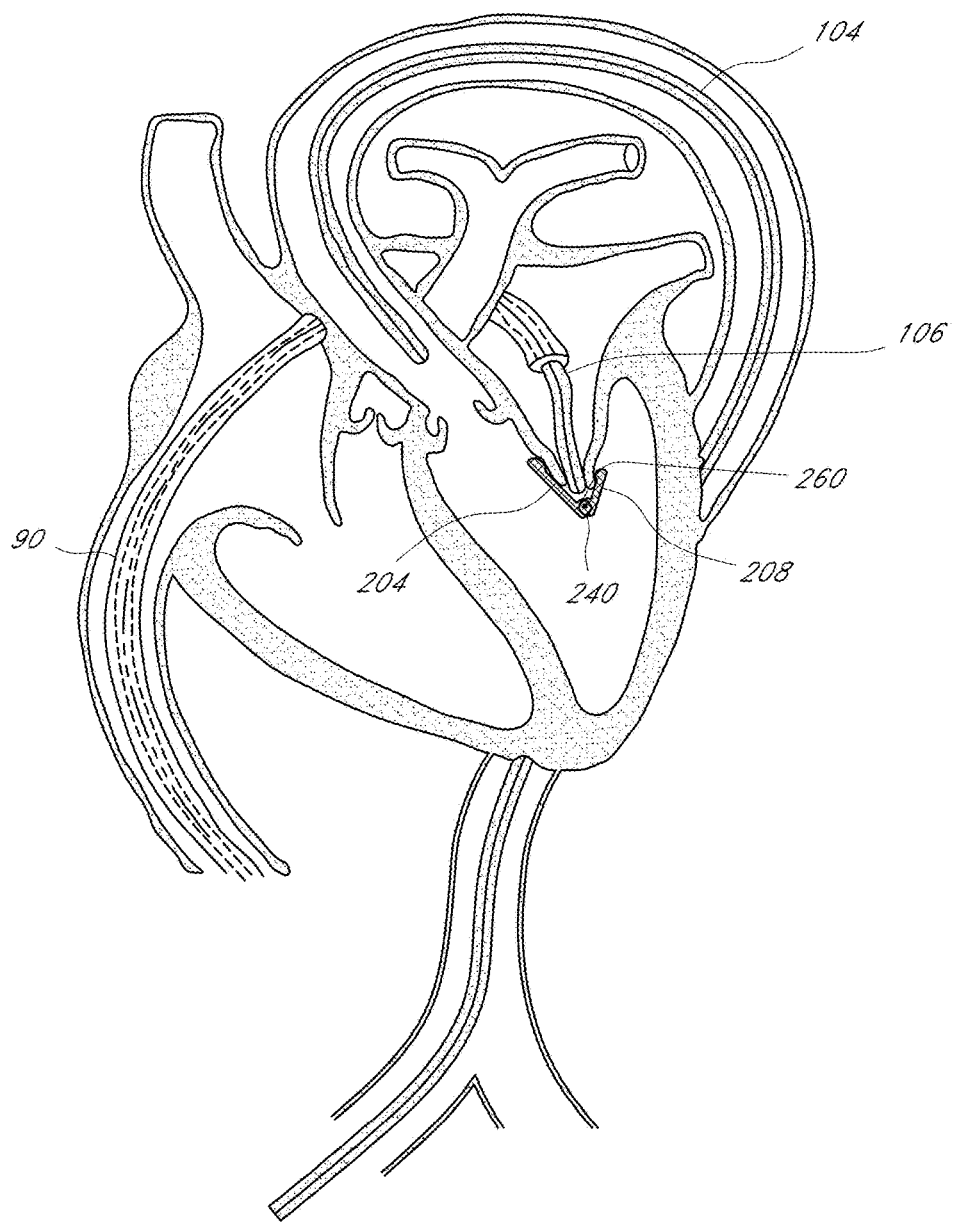
FIG. 8 is an image similar to that of FIG. 4, showing release of a distal portion of a delivery device from the valve treatment device, just prior to removal of the distal portion from the patient.

FIG. 8 shows that after the leaflets 3, 4 are captured, the valve repair device 200 can be de-coupled form the catheter 100 and left in place. The catheter 100 is then removed from the first and second access sites. In an initial decoupling step, the distal portion 104 of the catheter 100 can be decoupled from a distal interface 240 of the valve repair device 200 as described further below in connection with FIG. 10.

Figure 9:
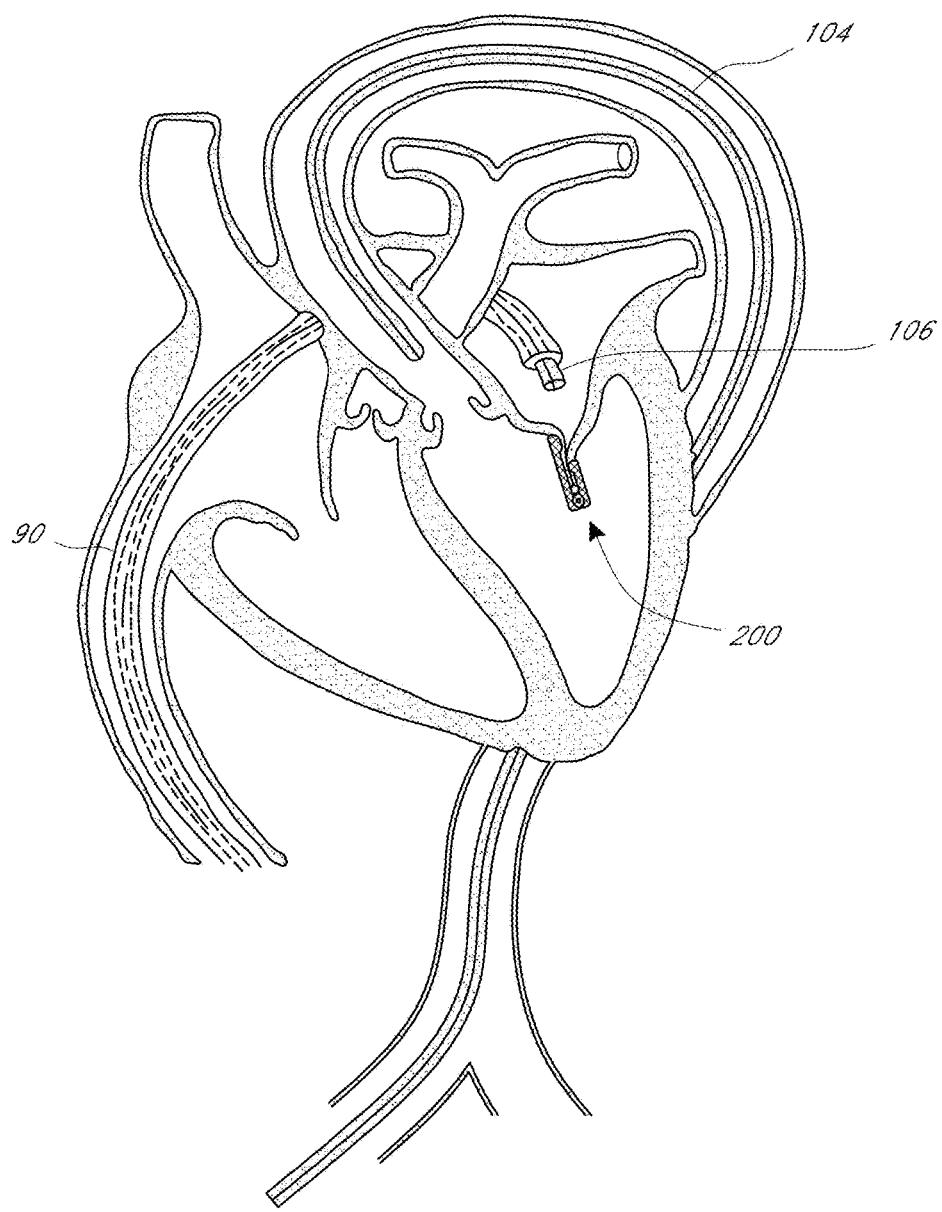
FIG. 9 is an image similar to that of FIG. 4, showing release of a proximal portion of a delivery device from the valve treatment device, just prior to removal of the proximal portion from the patient.

FIG. 9 shows that after the distal portion 104 is de-coupled from the valve repair apparatus 200 the proximal portion 106 can be de-coupled from the valve repair apparatus 200 as well. FIGS. 9 and 10 illustrate a proximal interface 260 that enables the valve repair apparatus 200 to be selectively separated from the proximal portion 106 of the catheter body. A variety of devices can be used for the proximal interface 260.

II. Apparatuses Capturing and Holding Valve Leaflets

Further details of various implementations of the catheter 100 are discussed with reference to FIGS. 10 through 14. In one embodiment, the catheter 100 can include a device housing catheter 400 made of material flexible and torqueable, preferably of a polymeric material but any other biocompatible material may be used. The device housing catheter 400 contains a central lumen through which the valve repair deployment catheter 404 can be advanced, and has in its wall holes 408, 412 (herein referred to as "portals") that, once the housing catheter 400 is in place in the ascending aorta with the assistance of the orientation catheter, are specifically aligned with the locations of the anterior leaflet 3 and posterior leaflet 4 to allow for the deployment of the anterior and posterior elements 204, 208 incorporated into the deployment catheter 404 that unfold and project out of the apparatus to gather the individual leaflets, as discussed above. FIGS. 11-14 show that the mitral valve repair device 200 can include anterior and posterior atrial elements 204A, 208A for provide enhanced security of each leaflet. The housing catheter 400 can be configured to deploy the elements 204A, 204B through the same or different portals as the elements 204, 208. The deployment catheter 404 is a catheter with a central lumen for a guide wire G, is made of material flexible and torqueable, and has a semi-rigid portion that contains the valve repair device 200. As discussed above, the valve repair device 200 includes anterior and posterior elements 204, 208 and the spring hinge 218, and in some cases the atrial elements 204A, 204B. In an alternative embodiment, the housing catheter 400 and deployment catheter 404 may be incorporated into a single catheter with a movable core and may contain a central lumen for a guide wire.

Monitoring the advancement and manipulation of the device housing catheter 400 and the deployment catheter 404 may be done by a variety of visualization techniques including, but not limited to MRI, fluoroscopy, endoscopy, thoracoscopy, transthoracic, intracardiac, and transesophageal echocardiography. These and other visualization techniques are employed throughout the present invention to track the movement of the apparatus inside a human body.

FIG. 10-14 depict in longitudinal section one embodiment of the present invention for mitral heart valve repair showing the housing catheter 400, advanced through a sheath 90 placed as depicted in FIG. 3, over a guide wire and into the proper position between the mitral valve leaflets 3 and 4. The deployment catheter 404 with its incorporated valve repair device 200 has been advanced over a guide wire through the device housing catheter 400 and into proper position with respect to the mitral valve leaflets 3 and 4. Through advancement, retraction, and torquing of the deployment catheter 404 by the operator, the deployment catheter allows the operator to manipulate the valve repair device. The function of the leaflet immobilization apparatus (including the anterior posterior elements 204, 208, spring hinge 218, and atrial elements 204A, 204B if present) is to clip or attach the anterior and posterior leaflets 3, 4 together. These components of the leaflet immobilization apparatus are preferably made of a sterile, biocompatible material such as a metal or plastic material known to be biocompatible. The leaflet immobilization apparatus is preferably cylindrical in shape, but may also be rectangular, conical or a multitude of other shapes. In mitral heart valve repair, the anterior element 204 may be longer than the posterior element 208, thus taking into account the anatomical difference in the size and shape of an anterior mitral valve leaflet 3 compared to a posterior mitral valve leaflet 4 as demonstrated in FIG. 2. By way of example, the shape of the anterior and posterior elements 204, 208 may resemble thin rectangular arms or wings that are connected by the hinge 218. However, the design of the anterior and posterior elements 204, 208 may be shaped in a variety of different forms. For example, the anterior and posterior elements 204, 208 may be circular, triangular, square, oval, or elliptical. The anterior and posterior elements 204, 208 may also be straight or curved. A cylindrical valve repair device with circular elements is discussed more in connection with FIGS. 16-20 below.

Differences in the sizes of the anterior and posterior elements 204, 208 may be tailored to the anatomical requirements of a particular surgical repair and patient. In any case, the shape of the anterior and posterior elements 204, 208 are designed to fit within the lumen of a catheter and, when deployed, to optimally interface with the unique anatomical shape of the anterior leaflet 3 and posterior leaflet 4, respectively. When the anterior and posterior elements 204, 208 are located outside the lumen of the catheter, the spring hinge 218 connecting the anterior and posterior elements 204, 208 extends the anterior and posterior elements 204, 208 outward and away from catheter system. The spring hinge 218 limits the range of movement of the anterior and posterior elements 204, 208 from a closed position, or zero degrees, to an open position not to exceed 90 degrees away from the catheter system. The spring hinge 218 exerts relatively little force against the anterior and posterior elements 204, 208 in the open position. When the anterior and posterior elements 204, 208 are contained within the lumen of the 400, the walls of the lumen force the anterior and posterior elements 204, 208 inward. In an alternative embodiment, the closed position of anterior and posterior elements 204, 208 may be maintained by a latch mechanism that can be released by an actuator in the proximal portion of the deployment catheter 404. Thus, in the lumen of the housing catheter, the anterior and posterior elements 204, 208 are flush within the housing catheter 400, and the spring hinge 218 is loaded with the force of the anterior and posterior elements 204, 208 in a closed position. To ease advancement of the deployment catheter 404 with its incorporated leaflet immobilization apparatus, the housing catheter 400 may contain grooves shaped to receive the anterior and posterior elements 204, 208, or to receive the deployment catheter 400 in a proper orientation so that the anterior and posterior elements 204, 208 are directed properly toward the portals 408, 412 in the housing catheter 400. In an alternative embodiment, the housing catheter 400 and the deployment catheter 404 with its incorporated leaflet immobilization apparatus may be incorporated into a single catheter with a moveable core that allows for the manipulation of the anterior and posterior elements 204, 208, the spring hinge 218, and atrial element 204A, 208A by actuator or actuators at the proximal end of the catheter system, or by direct manipulation of the core itself at the proximal end of the catheter system.

FIG. 10 thus depicts the deployment catheter 404 advanced within the housing catheter 400 and the anterior and posterior elements 204, 208 in closed positions. The deployment catheter 404 has been advanced within the housing catheter 400 so that the anterior and posterior elements 204, 208 are positioned below the ventricular aspect of the open anterior 3 and posterior 4 leaflets. The anterior and posterior elements 204, 208 are now ready for deployment.

FIGS. 10-13 sequentially depict one embodiment of independent deployment of anterior element 204. In FIG. 10 the deployment catheter 404 is shown advanced toward the distal end of the housing catheter 400 that has an anterior portal 208. The proximal end of deployment catheter 404 may extend outside the proximal end of the housing catheter 400. This enables the operator to push and pull the deployment catheter 404 in a distal or proximal direction within the catheter. As the operator pulls the catheter 404 in the proximal direction, the valve repair device (including of the anterior and posterior elements 204, 208, and the spring hinge 218) moves in a proximal direction within the housing catheter 400. In addition, gradually, the anterior element 204 independently extends outward from the anterior portal 408 as the entire length of the anterior element 204 moves proximally toward the open space of the anterior portal 408 of the housing catheter's 400. The anterior element 204 independently extends outward first because of the differential lengths of anterior element 204 and posterior element 208 and because of the differential locations of the anterior portal 408 and the posterior portal 412. Without the containment of the lumen walls of the housing catheter 400, the force of the loaded spring hinge 218 extends the anterior element 404 through the anterior portal 408 of the housing catheter 400 away from the deployment catheter 404.

Figure 12:
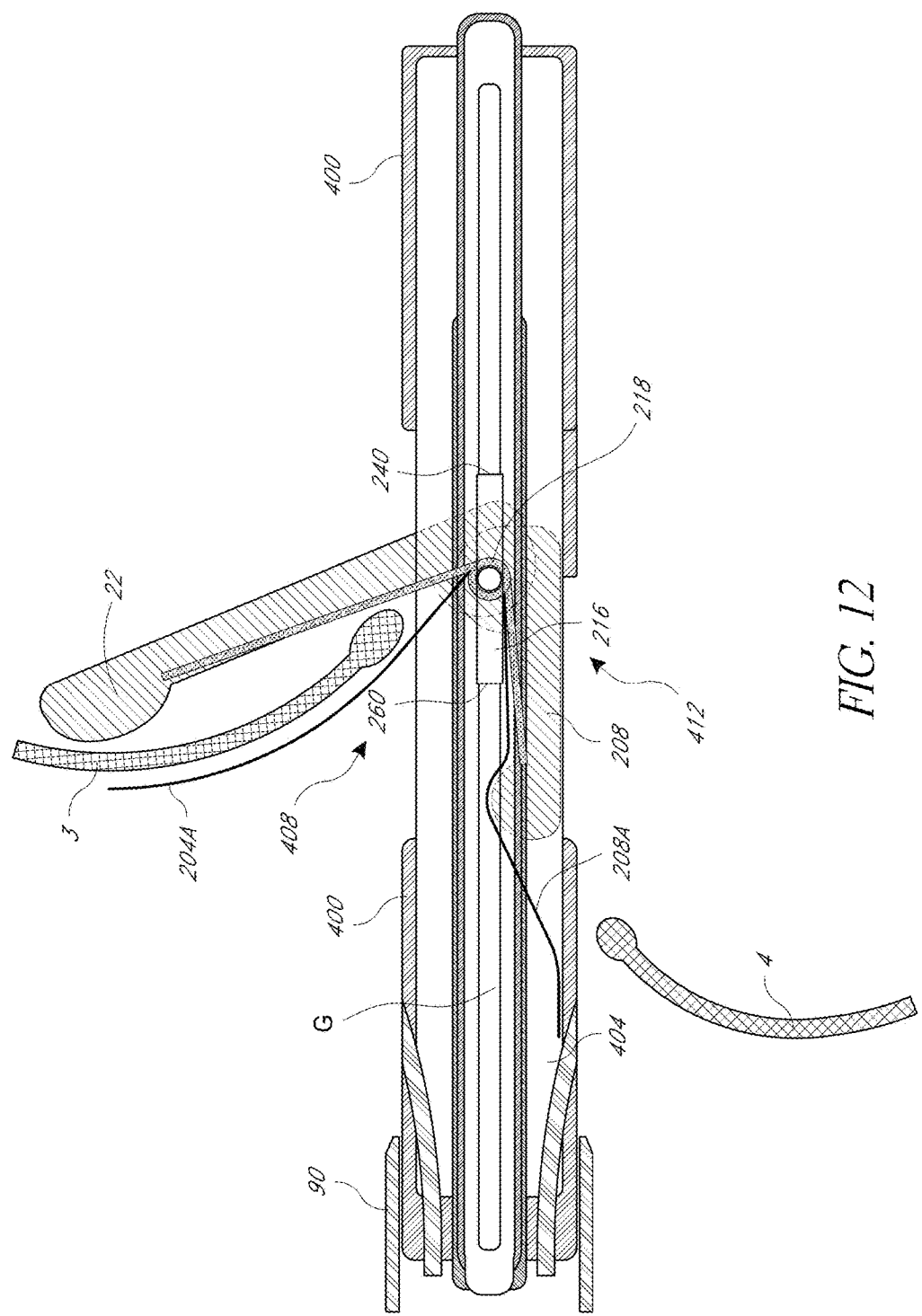

In an alternative embodiment, an operator may release the anterior element 204 or actuate the deployment of the anterior element 204 by way of an actuator located at the proximal end of the deployment catheter 400. Referring back to FIG. 1, the tips of the mitral valve leaflets 3 and 4 point in a ventricular direction when open. Thus, the angle of the deployed anterior element 204 allows for the engagement of the ventricularly directed anterior valve leaflet 3. Incorporating FIG. 1's frame of reference regarding the mitral valve leaflets 3 and 4, FIG. 11 shows the anterior element 204 free from the lumen of the housing catheter 400 and in a partially extended position below the anterior mitral valve leaflet 3. FIG. 12 next shows the anterior element 204 in a fully extended position below the anterior leaflet 3, and engaging the anterior leaflet 3. Once the anterior element 204 is fully extended and positioned below the anterior leaflet 3, the flexible and torqueable nature of the housing catheter 400 and the deployment catheter 404 allow the operator to move and adjust the housing catheter/deployment catheter system until the anterior element 204 is determined to be positioned optimally below the anterior leaflet 3, using imaging techniques such as fluoroscopy, MRI, transesophageal, intracardiac, transthoracic, or three-dimensional echocardiography as needed.

The atrial element 204A, if present, can be deployed as illustrated in FIGS. 11 and 12. In particular in FIG. 11, the element 204A is retained within the housing catheter 400. Relative proximal movement of the housing catheter 400 moves the element 204A into the portal 408. When disposed in the portal the element 204A can swing open to the position shown in FIG. 12. Although spaces are shown between the element 204A and the anterior leaflet 3 and between the leaflet 3 and the anterior element 204, in various embodiments these structures are closely sandwiched together. In particular, the element 204A can be configured to be biased to swing oven to a larger extent than the element 204. However, due to the rigidity of the element 204, the element 204A will press up against and conform to the surface of the element 204. This will result in a force being applied to the leaflets. Although shown as smooth surfaces, one or both of the elements 204, 204A can have barbs or other structures suitable for enhancing engagement with the valve tissue. Some of such structures are set forth in the incorporated subject matter of the Appendix.

Figure 14:
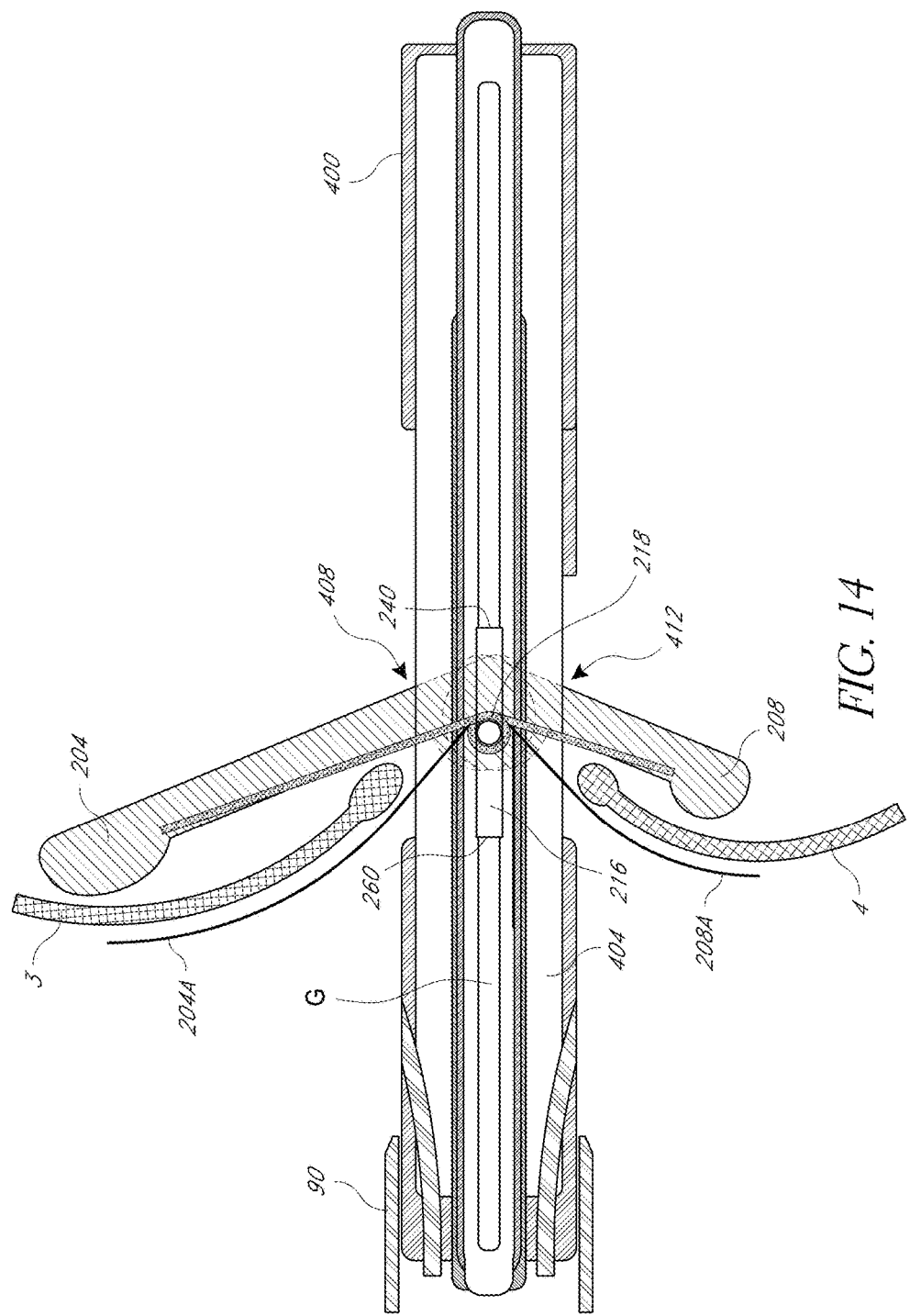
Figure 15:
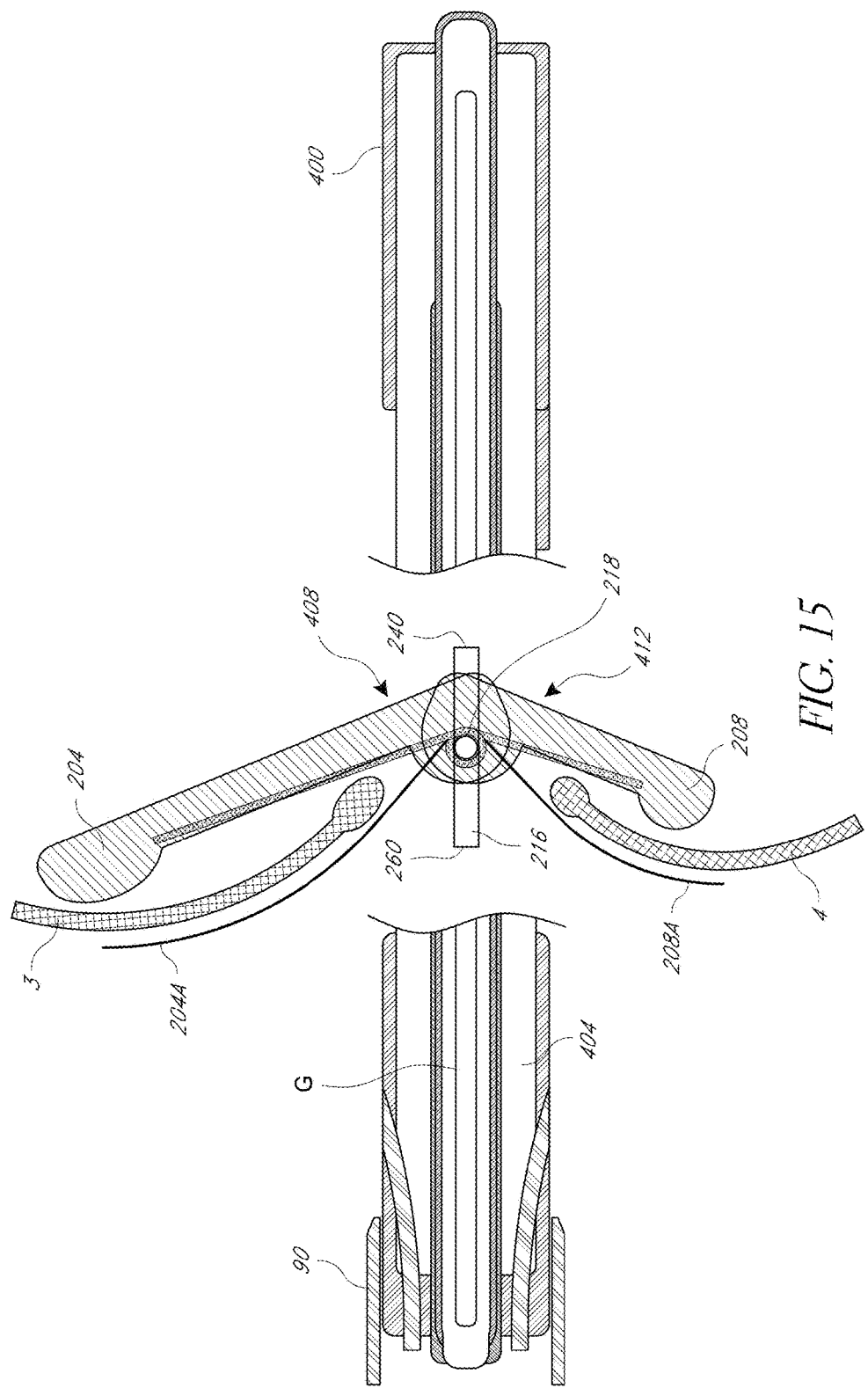

FIGS. 13 and 14 sequentially depict one embodiment of the present invention showing the independent deployment of posterior element 208. Once the anterior element 204 extends through the anterior portal 408, the operator may further pull the deployment catheter 404 in a proximal direction. This movement will cause the posterior element 208 to move in the lumen of the housing catheter 400 to the opening of the posterior portal 412. In one technique, the atrial element 208A may thereafter be deployed to sandwich the leaflet 4 between the elements 208, 208A. The posterior element 208 may be shorter than the anterior element 204 taking into account the size difference of the anterior leaflet 3 and posterior leaflet 4 of the mitral valve. Similar to the independent deployment of anterior element 204, the posterior element 208 gradually and independently springs to an open position as the operator pulls the deployment catheter 404 proximally. In an alternative embodiment of the present invention, an operator may actuate the release and/or deployment of the posterior element 208 by way of an actuator located at the proximal end of the deployment catheter 404. In FIG. 13, the posterior element 208 is shown in a partially extended position shortly after clearing the lumen of the housing catheter 400 through the posterior portal 412. Similar to anterior element 204 positioning, the posterior element 208 is positioned at the ventricular side of posterior leaflet 4. In FIG. 14, the posterior element 208 is in a fully deployed position and is optimally positioned under posterior leaflet 4.

The atrial element 208A, if present, can be deployed as illustrated in FIGS. 13 and 14. In particular in FIG. 13, the element 208A is retained within the housing catheter 400. Relative proximal movement of the housing catheter 400 moves the element 208A into the portal 412. When disposed in the portal the element 208A can swing open to the position shown in FIG. 14. Although spaces are shown between the element 208A and the posterior leaflet 4 and between the leaflet 4 and the anterior element 208, in various embodiments these structures are closely sandwiched together. In particular, the element 208A can be configured to be biased to swing oven to a larger extent than the element 208. However, due to the rigidity of the element 208, the element 208A will press up against and conform to the surface of the element 208. This will result in a force being applied to the leaflets. Although shown as smooth surfaces, one or both of the elements 208, 208A can have barbs or other structures suitable for enhancing engagement with the valve tissue. Some of such structures are set forth in the incorporated subject matter of the Appendix.

III. Structures for Distal Release of a Valve Repair Device

The distal and proximal interfaces 240, 260 are shown in only some of the figures for the sake of keeping the other drawings simpler. These structures and the hub 216 of which they are a part, or an analogous variation, can be present in the embodiments illustrated in the other figures as well. Preferably the distal interface 240 is one that is secure but configured to detach the distal portion 104 of the catheter 100 from the repair apparatus 200. In one embodiment, the distal portion 104 includes an outer catheter body that extends between the distal end of the distal portion and a proximal end of the distal portion. Inside the catheter body, a lumen carries an inner sleeve that bridges between the distal interface 240 and the proximal end of the catheter body. The inner sleeve can comprise and an elongate body that has in outer surface that slideably engages the inner lumen of the catheter body. If the distal portion 104 is to be delivered over a guidewire, the inner sleeve can include an elongate lumen extending therethrough from the distal end of the distal portion 104 to the proximal end of the distal portion.

To detach the distal portion 104 from the distal interface 240 of the valve repair apparatus 200 one can provide distal relative movement of the inner sleeve relative to the catheter body of the distal portion 104. This removes the unifying force of the inner sleeve and permits the distal interface 240 to separate from the proximal end of the distal portion 104. For example, a lateral movement of the proximal end of the distal portion 104 relative to the distal interface 240 can separate these structures from each other permitting the distal portion to be withdrawn. In another embodiment, the inner sleeve can be provided on the outside of the proximal end of the distal portion 104 and can extend proximally of the distal interface 240.

Many variations of mechanisms to deploy devices are discussed in U.S. Pat. No. 8,216,256, which is hereby incorporated by reference herein in its entirety.

The proximal interface 260 can be configured similar to the distal interface 240 or as discussed in the '256 patent or can have another configuration. In one variation, the proximal interface 260 operates by providing a torque to a proximal structure carried by the proximal portion 106 of the catheter 100. In particular, the proximal portion 106 can include a catheter body with a lumen extending therethrough. A cylindrical sleeve can be disposed within the lumen of the catheter body. The sleeve can be configured to securely retain the valve repair apparatus 200 at the proximal interface 260. For example, the proximal interface 260 can include a tubular body disposed on the central hub 216 having internal threads disposed thereon. The distal end of the inner sleeve can be threaded to match the internal threads of the proximal interface 260. Accordingly, relative rotation of the inner sleeve relative to the catheter body of the proximal portion 106 can result in separation of the valve repair apparatus 200 from the proximal portion 106. Further details of threaded connections for detaching deployable devices within a body lumen or cavity are discussed in U.S. Pat. No. 7,226,467, which is incorporated by reference herein.

Among the many variations, the structures for disconnecting the valve repair apparatus 200 from the proximal and distal aspects of the catheter 100 can be of the same type. The structures described as being used for the proximal interface 260 can be used for the distal interface 240, and those described for the distal interface can be used for the proximal interface.

The procedure may be or may include a diagnostic procedure. It may comprise an imaging procedure, or a hemodynamic monitoring procedure. For example, an imaging device 500 can be disposed in the catheter 100. The imaging device 500 includes an ultrasound transducer 504 and a movement device 508 coupled with the transducer 504. The movement device 508 enables the transducer 504 to move relative to the procedures zone 120 such that a segment of the anatomy along the procedure zone can be imaged. In one example, the movement device 508 comprises a rotatable member that is disposed in the lumen 130. The rotation enables the transducer 504 to obtain imaging data about the catheter 100. FIG. 10 shows the movement device 508 positioned inside the guidewire G. In variations, the guidewire and the movement device 508 can be positioned sequentially, for example removing the guidewire G prior to the insertion of the movement device 508. In other embodiments, separate lumens are provided for the guidewire G and the movement device 508 within the catheter 100. Preferably the movement device 508 is also able to translate to move the transducer axially to provide imaging along a length. An example of an imaging device is discussed in US 2006/0259137 A1, published November 2006, which is incorporated by reference herein.

The movement device 508 can be configured to be operated from either one or both of the first and second access sites discussed above. For example, one or both of the distal end and the proximal end of the translation device 508 can be configured to be coupled with an actuator to provide rotation and/or translational movement of the transducer 504. In various methods the transducer is advanced from the arterial access site to a location upstream of the valve being treated. An anatomical segment including, for example, the mitral valve is imaged from upstream to downstream. Thereafter an appropriate step is taken, such as a medial-lateral adjustment of the position of the valve repair device 200 along the valve. For example, with respect to FIG. 4A, the catheter can be torqued to move the device 200 closer to the center of the box C. The imaging device 500 is then withdrawn toward the arterial access site so that the repair device 200 can be detached from the distal portion 104. Thereafter, the distal portion 104 and the imaging device 500 can be removed from the arterial access site, either together or sequentially.

A similar approach could be directed form the venous access site. In this approach, the imaging device 500 can be advanced through the catheter 100 to the just proximal of the valve. Then, the imaging device 500 can be activated to gather imaging data, for example while rotating and traversing a valve and an adjoining anatomical region of interest. Thereafter the imaging device 500 is withdrawn to a location proximal of the repair device 200 so that the repair device can be separated from the proximal portion 106 of the catheter 100. Subsequently, the proximal portion 106 and the imaging device 500 are withdrawn together or sequentially.

IV. Enhanced Valve Prostheses

FIGS. 16-19 illustrate further embodiments of implants having improved coupling with valve leaflets. In particular, FIGS. 16-19 show a valve repair prosthesis 600 with curved leaflet grasping elements. The prosthesis 600 is configured to be deployed from a catheter assembly or system, such as the catheter 100 or the catheter system 800 shown in FIG. 20. As discussed above, the catheter 100 can be delivered over a guidewire. Similarly, the prosthesis 600 can have a lumen (not shown) extending entirely therethrough for passage of a guidewire. Or, a side lumen may be provided on the catheter 100 such that no dedicated guidewire lumen is provided on the prosthesis.

The prosthesis 600 comprises a prosthesis body 604 that extends between proximal and distal ends 608, 612. Some or all of the prosthesis body 604 can be metallic, e.g., a biocompatible metal. Suitable metals include any one of or any combination of nickel, titanium, stainless steel and other biocompatible radiopaque metals and materials. The prosthesis 600 comprises a base 616 in a central position and a plurality of grasping element 620, 624 disposed laterally of the base 616. The grasping elements 620, 624 can be identical, but in certain embodiments are asymmetrical such that the grasping element 620 is a posterior element and the grasping element 624 is an anterior element. The posterior element 620 may be configured specifically configured to better grasp the anterior leaflet 3. The anterior element 624 may be configured specifically configured to better grasp the posterior leaflet 4. Each of the grasping elements 620, 624 can include an elongate member articulated to the body 604 and thus may be considered to be arms of the prosthesis 600.

The prosthesis 600 is elongate in certain embodiments, e.g., having a larger longitudinal dimension between the proximal and distal ends 608, 612 than a dimension transverse to the longitudinal dimension. The prosthesis 600 has a generally cylindrical configuration with a circular profile in transverse cross-section (taken perpendicular to a longitudinal axis). The cylindrical profile enables the prosthesis 600 to rotate in a catheter system or in a sheath, such as any of the catheter systems discussed herein, to orient the prosthesis circumferentially in the catheter system or sheath. This allows the rotational position of the prosthesis 600 to be changed within a circular lumen of a delivery catheter or sheath, e.g., to rotate the grasping element 620, 624 toward or away from windows or portals in the catheter body 100.

The posterior and anterior elements 620, 624 are coupled with the central base 616. In certain embodiments, the posterior element 620 can be coupled with the base 616 at a distal portion thereof. A hinge connection 632 can be provided between a distal portion 636 of the posterior element 620 and a distal portion 638 of the base 616. Similarly, the anterior element 624 can be coupled with the base 616 at a distal portion 640 thereof. A hinge connection 644 can be provided between a distal portion 648 of the anterior element 624 and the distal portion 652 of the base 616.

The hinge connections 632, 644 advantageously are disposed away from each other to help maintain the small size of the prosthesis. In certain embodiment, the hinge connection 632 to the posterior element 620 is disposed at a single location adjacent to the distal end 612 at a first position of the circumference of the prosthesis 600. In certain embodiment, the hinge connection 644 to the anterior element 624 is disposed at a second position adjacent to the distal end 612 of the prosthesis 600. The first and second positions preferably are offset by at least 45 degrees and in some cases 90 degrees or more. The hinge connection 644 can include a plurality of pivot points, e.g., one on each side of the prosthesis 600.

In one embodiment, the anterior element 624 is disposed on a first side of the prosthesis and the posterior element 620 is disposed on a second side of the prosthesis opposite the first side. By positioning the elements on opposing sides, the elements 620, 624 are configured to have their point of largest movement in a plane transverse to the line of coaptation of a valve when applied. The anterior element 624 can have a hinge connection 644 that includes two pivot points on opposite sides of the prosthesis 600. The hinge connection 632 to the posterior element 620 can be at a single location spaced apart from one or both connection points of the hinge connection 644.

Figure 16:
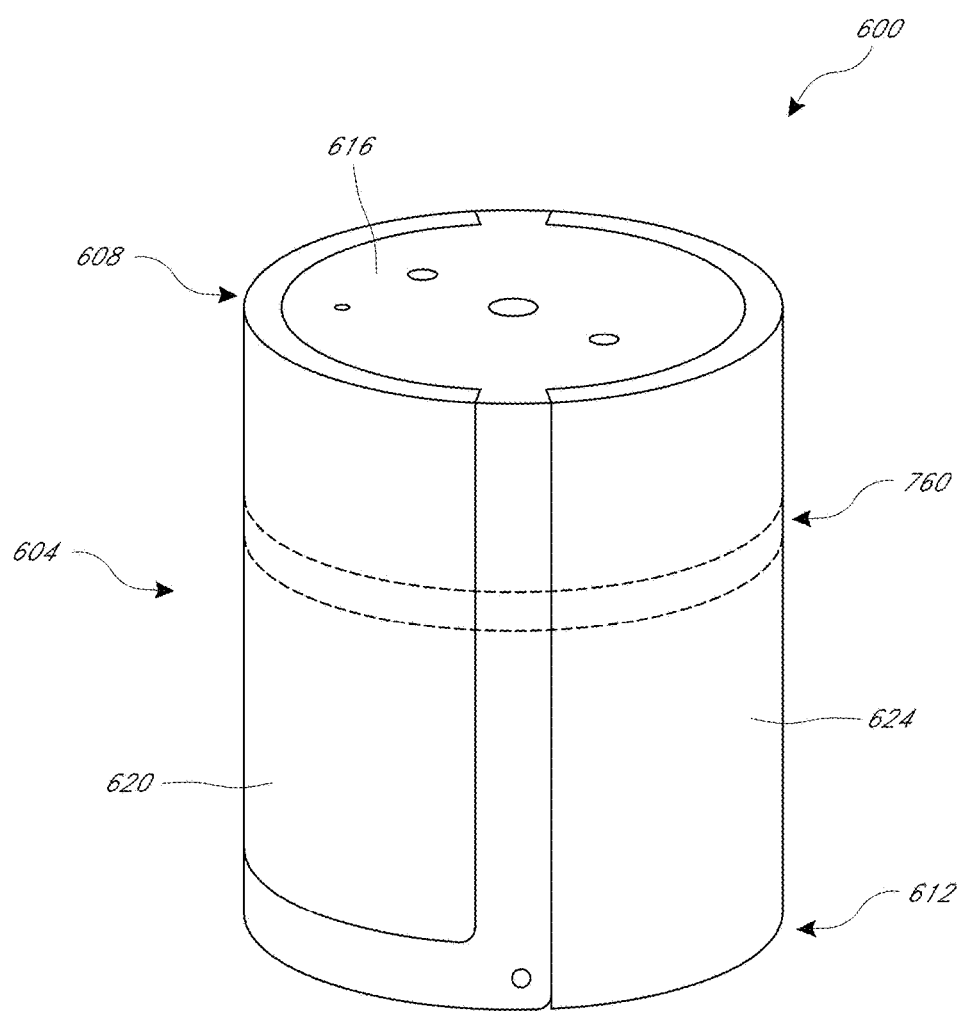
FIGS. 16-19 illustrate aspects of valve prostheses that enhance coaptation compared to conventional prostheses.
Figure 17:
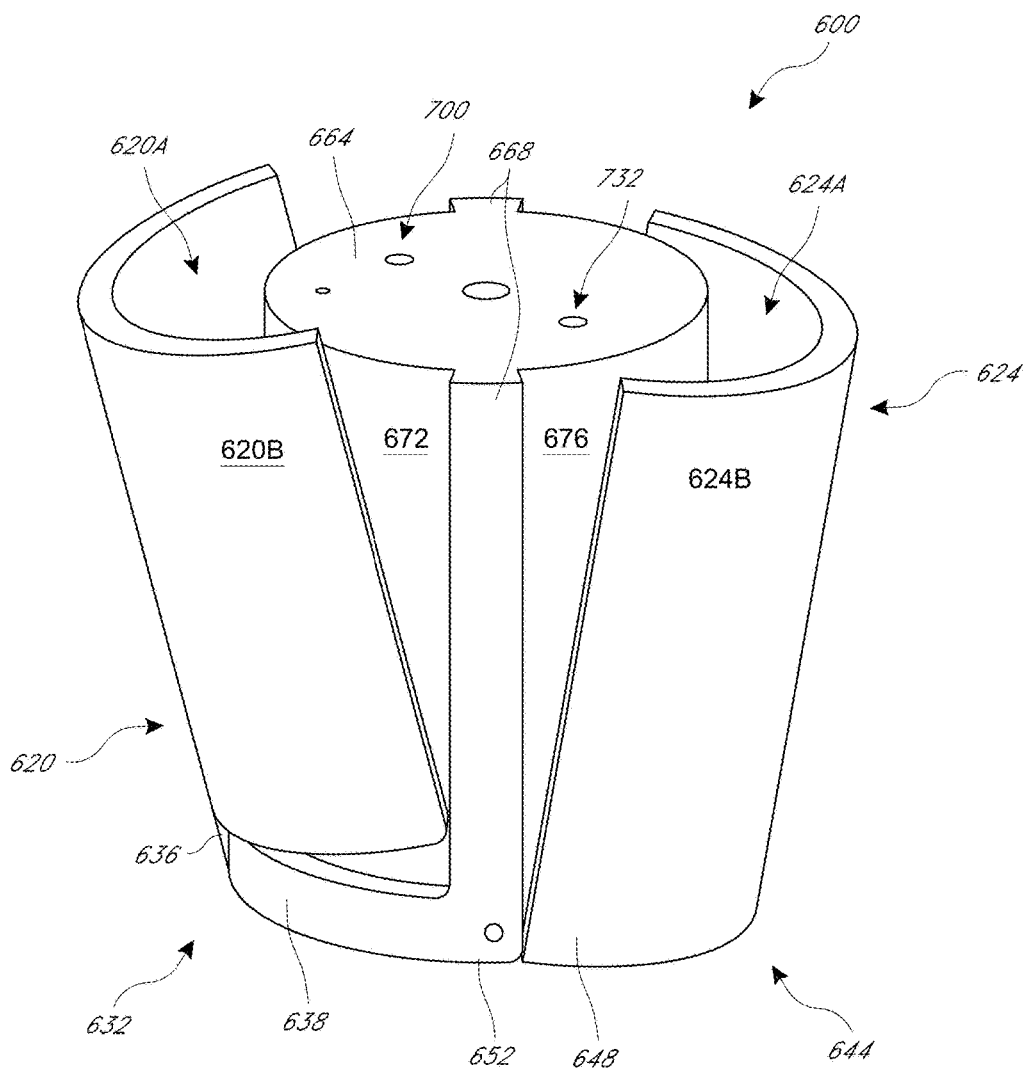

The prosthesis 600 is configured such that the hinge connections 632 644 move the grasping elements 620, 624 from a closed position (FIG. 16) to an open position (FIG. 17). In the open position the elements extend away from the base 616 at least at a proximal ends thereof. In the closed position the element 620, 624 are in a flush position relative to the base 616. The base 616 can be configured to facilitate the flush arrangement. For example, the base 616 can include a substantially cylindrical core 664 with lateral protrusions 668 extending from a periphery of the core 664. The protrusions 668 can extend longitudinally along at least a portion of, e.g., along the entire core 664. In one embodiment, the protrusions 668 comprise a flange on one or both sides of the core 664. The core 664 can have a first outer surface 672 matching an inner side 620A of the posterior element 620 and a second outer surface 676 matching an inner side 624A of the anterior element 624. The matching surfaces enable the elements 620, 624 to rest very close to the base 616 providing little or no gap therebetween in the closed position. A proximally facing shoulder extending from the lateral protrusions circumferentially toward the hinge connection 632 has a radial with that is about the same as the thickness of the anterior element 624 such that the element 624 is received in a flush arrangement relative to the shoulder.

One or both of the surfaces 620A, 624A are textured, coated, or otherwise processed to maximize frictional engagement with the leaflet tissue. One or both of the surfaces 672, 676 are textured, coated, or otherwise processed to maximize frictional or other engagement with the leaflet tissue. The surfaces on the outer sides 620B, 624B preferably are flush with the radially outer surface of the protrusions 668 of the core 664 in the closed position. This arrangement facilitates reducing or minimizing the size of the delivery catheter by reducing or minimizing gaps between the outer surfaces 620B, 624B and the inner wall of the catheter body in which the prosthesis 600 resides.

Figure 18:
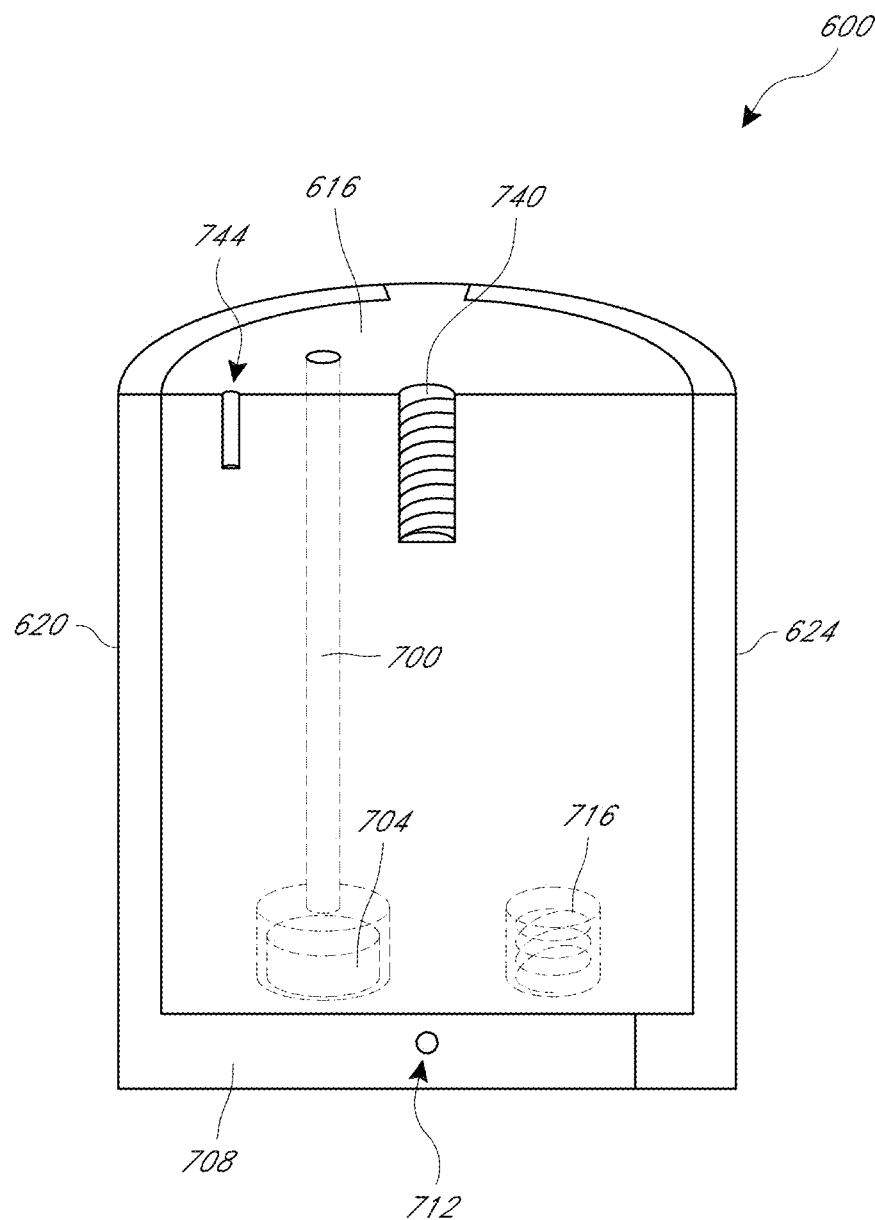

The prosthesis 600 is configured such that the posterior and anterior elements 620, 624 can be actuated independently. Such actuation can be by any suitable mechanism or technique. In one embodiment, the posterior and anterior elements 620, 624 are actuated pneumatically. FIG. 18 shows that a control channel 700 can be provided in the base 616, e.g., in the core 664 to provide for remote control, e.g., actuation of the gripping elements 620, 624. For example, the control channel 700 can provide fluid communication between a source of control fluid and a distal end of the control channel 700, e.g., in a pneumatic or hydraulic configuration. This enables a driving fluid, which can include one or more of saline, water, heparin, radiopaque contrast, or other biocompatible liquid, to flow into the prosthesis 600. In certain embodiments, the control channel 700 is configured to convey within the prosthesis 600 a gas such as one or more of nitrogen, air, carbon dioxide, oxygen, or other gases that area highly soluble in blood or otherwise biocompatible. The control channel 700 could be coupled with a source of any of these control fluids or with other inert synthetic fluids, particularly those that have low toxicity and high solubility for gas, e.g., any suitable perfluorocarbon. In one embodiment, the channel 700 is in fluid communication with an actuator 704 disposed at the distal end of the channel 700. The actuator 704 can be or can comprise a portion of a piston. A distal face of the actuator 704 is engaged with or is in position to drive a portion of the posterior element 620. In one embodiment, the distal portion of the posterior element 620 comprises a flange 708 that extends from the outer periphery of the prosthesis across the distal end of the prostheses 612 to a pivot 712. The actuator 704 is configured to act on the flange 708 at a location between the pivot 712 and the outer periphery of the prosthesis 600.

The control channel 700 could be configured to have mechanical control elements disposed therein. For example, the actuator 704 can be engaged with a wire or other compression or tension member that is able to push on the actuator. As the compression or tension member is moved in the control channel 700 the actuator 704 acts on the flange 708 in certain embodiments. In certain embodiment, a compression or tension member (e.g., a wire) is directly engaged with the flange 708 or another part of the gripping element 620 to directly actuate the element 620. The compression or tension member (e.g., a wire) preferably is able to be disengaged from the prosthesis 600 upon release of the prosthesis from the catheter assembly in which it is delivered.

Figure 19:
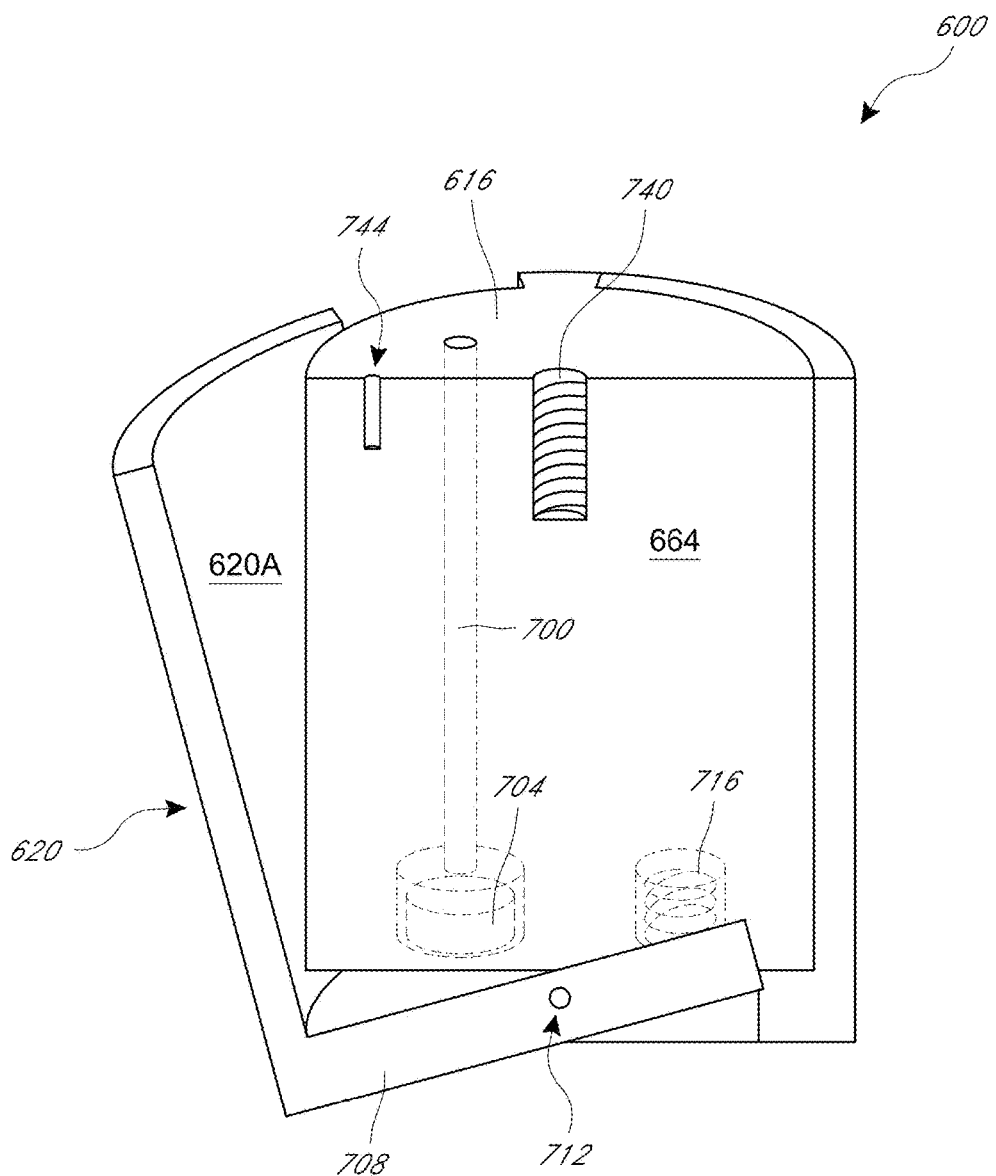

The posterior element 620 can be configured to be biased toward the closed position of FIGS. 16 and 19. In one example, a spring 716 is provided between the posterior element 620 and a portion of the prostheses to push the posterior element 620 toward the close position, e.g., to push the surface 620A toward and into engagement with the outer surface 672.

Although the details of the structures for actuating the anterior element 624 is not shown in cross-section, the anterior element can be actuated in a manner similar to the posterior element 620. In particular, a channel 732 can be provided that opens to the proximal end 604 of the prostheses. The channel 732 can communicate with another actuator similar or the same as the actuator 704 to move the surface 624B away from the surface 676. The anterior element 624 can be biased toward the closed positions of FIGS. 16 and 18 by a spring or other biasing member.

The prosthesis may also have features for connecting the prosthesis 600 to a catheter or catheter system 800 (see FIG. 20) or the catheter 100 described herein. For example, the prosthesis 600 may have a threaded recess 740 extending from the proximal face of the base 616. The threaded recess 740 enables connection to a catheter device or system, such as a pusher disposed in a catheter body. The pusher can help in positioning the prosthesis at the mitral valve for example. The prosthesis 600 also can have an indexing feature 744 configured to align the prosthesis 600 in a specific orientation relative to a catheter body in which the prosthesis is delivered. In one form, the indexing feature 744 comprises a recess configured to receive a pin or other protrusion of a delivery catheter. The indexing feature 744 can be a blind hole. In some embodiments the indexing feature 744 includes threads or other engagement features. In some embodiments the indexing feature 744 is able to both index the orientation of the prosthesis 600 relative to a catheter body and to releasably secure the prosthesis during delivery.

In certain embodiments, the prosthesis 600 is configured to be indexed to a catheter body without a dedicated indexing recess. Reducing the number of recesses or eliminating them completely can improve the biocompatibility of the prosthesis 600. For example, reducing or eliminating such features can reduce the chance of embolism because recesses may be a site for blood clot formation. Thus the indexing feature can include structures such as matched surface contours, temporary or low to moderate strength adhesives, frictional engagement, paired permanent magnets, and other engagement features. Matched surface contours can include a convex surface (e.g., on the proximal end 608 of the prosthesis body 604) and a concave surface (e.g., on the distal portion of a catheter body component disposed to engage the proximal end 608). The concave and convex surfaces can be configured with local apices offset from the geometric center of the proximal surface of the core 664.

Another use of these indexing features is to provide a counter-force in disengaging the prosthesis 600 from a catheter system in which it is delivered. In certain embodiments, the threaded recess 740 is unscrewed from a threaded member disposed in a catheter assembly used for delivering the prosthesis 600. The indexing feature 744 can provide a counter-force in certain embodiments. That is, an indexing structure of a catheter assembly engaged with the indexing feature 744 applied a torque opposing the torque generated by backing the threads of the catheter assembly threaded member out of the threads of the threaded recess 740.

Although not shown, the distal end 612 of the prosthesis 600 can also include and indexing feature and/or a threaded recess. A distal threaded recess can enable detachment of a threaded member extending in the distal portion 104 of the catheter 100 in the manner discussed above or from the catheter system 800. A distal indexing feature can be used for counter torque when a threaded member is detached from a distal threaded recess. In some techniques the indexing feature 744 can be used for counter torque when a threaded member is detached from a distal threaded recess. In other variations, the indexing feature 744 is omitted and an indexing feature is disposed only on the distal end 612 of the body 604.

FIG. 16 shows that the prosthesis 600 can include as a further optional feature a retention member 760 configured to be disposed about the body 604. The retention member 760 is shown in dashed lines for clarity. In some embodiments, the retention member is provided to enhance the security of the grasping elements 620, 624 when the prosthesis is applied. The retention member 760 can be an elongate elastic member that can be stretched to be moved over the outside of the body 604. The elasticity of the member 760 is preferably sufficient to apply a circumferential compressive force onto the outer surface of the grasping elements 620, 624. The compressive force is sufficient to increase the forces applied by the grasping elements 620, 624 to a layer of valve tissue disposed between the faces 620A and 672 and/or the faces 624A and 676.

The retention member 760 can be disposed on either the proximal or distal portion of the catheter 100. For example, in one embodiment, the retention member 760 is dispose don the distal portion 104 and can be urged over the distal end 612 of the body 604 after the leaflets 3, 4 have been grasped. Transferring the retention member 760 from an outside surface of the distal portion 104 onto the outside surface of the body 604 can be accomplished in any manner. For example, the distal portion 104 can include a sheath disposed over an inner body. The sheath can have an end closes to the prosthesis 600. The end can abut an end of the retention member 760. The abutting relationship will provide that as relative motion is provided between the sheath and the inner body (e.g., the sheath urged toward the mitral valve leaflets, the retention member 760 will also be urged off of the inner body and onto the body 604 of the prosthesis 600. In another embodiment, the retention member 760 can be disposed in or on the portion 106. The retention member 760 can be disposed on an outside surface of the proximal portion 106 and can be urged distally by a sheath disposed around the outside surface.

The prosthesis 600 can be positioned at a heart valve, e.g., within the mitral valve, using a wire or catheter guidance rail that is fixed at both ends in a position external to the body, as discussed above. The placement can be facilitated by providing both venous and arterial placement. In one technique, initial placement is provided similar to FIG. 3. For example, access is provided to a peripheral venous site. Any standard technique can be used to cross the atrial septum. For example, a guide catheter or sheath 90 can be provided. Alternatively, a proximal portion can have a obturator or dilator for passing the proximal segment through the atrial septum.

The venous segment is then advanced across the mitral valve into the left atrium, through the left ventricle, across the aortic valve, and through the ascending and descending aorta away from the heart. The venous segment, which may be similar to the proximal portion 106, may include one or more internal lumens to facilitate injection of pharmaceutical or contrast agents or passage of a guidance wire, and may include structural features intended to allow the tip to be directed by blood flow such as a balloon, as discussed above.

An arterial segment can be provided by a suitable technique. For example, FIG. 3A shows an arterial segment 104A can be placed percutaneously through an arterial access site and advanced toward the distal tip 108A of the venous segment 106A. More generally, venous segment can be joined to a segment exiting the patient at a second site, which can be an arterial site as discussed elsewhere herein. The second site can be provided by a surgical procedure that may be minimally invasive. For example, access can be provided through a sub-xiphoid approach to the outside of the heart. A transapical channel can be formed from the outer apex of the heart to the left ventricle. The transapical channel can be disposed within a sheath that is placed through the myocardium. The channel can be of sufficient size for the segment 104A to extend therethorugh. Thus a continuous rail can be provided from the venous access site to the second site outside the patient through the sub-xiphoid access. While the transapical path does not benefit from the anatomical guidance discussed above in connection with FIGS. 1-3, the trajectory from the left atrium, through the mitral valve and out of the apex can be substantially straight in many patients and thus may provide good perpendicularity to the mitral valve annulus, which helps seat the prostheses discussed herein or even a stent mounted prosthetic valve in the mitral valve annulus. Further details of how one would provide transapical access to the left ventricle are discussed in WO2011/017440, which is incorporated by reference in its entirety.

A loop, snare, Shepard's hook tip or other structure for capturing the venous segment 106A can be provided on the arterial segment 104A. The capturing structure is provided such that the venous segment can be withdrawn percutaneously through the arterial access site to create a single, continuous, guidance rail extending from the venous access site, through the heart, to the arterial access site. In other approaches, the arterial and venous segments are joined intravascularly to provide a continuous venous-arterial guide rail. The guidance and ensnaring or joining method may be accomplished using mated surfaces such as a ball and socket, fixation methods or structures such as a threaded connector, or using permanent or electro-magnetically tipped segments that attract when in proximity. Portions of one or both of the tips of the segments 104A, 106A may be radiopaque to facilitate snaring of these components.

In further embodiments, using any one or combination of guidance technique, e.g., echocardiographic, fluoroscopic, or flow-directed guidance, the venous segment guidance rail is placed percutaneously through a venous access site, advanced across a atrial septal aperture, through the mitral valve, left ventricle, aortic valve, ascending aorta, aortic arch, and finally into the descending aorta. From an arterial access site, the arterial segment is placed percutaneously into an arterial access site, and advanced toward the distal tip of the venous segment. Utilizing a snare disposed on the arterial segment or other joining device such as permanent magnets embedded into the distal tips of both venous and arterial segments, the venous segment is ensnared firmly by the arterial segment. As the venous segment is advanced, the arterial segment is withdrawn to guide the venous segment toward and out of the arterial access site. This establishes a continuous guidance rail extending percutaneously from the venous access site to the arterial access site. Or, as noted above, the venous and arterial segments may be joined by permanent magnets, a threaded connection or other low profile joining structure such that the venous and arterial segments can remain in place for advancement of other catheter devices thereover.

Figure 20:
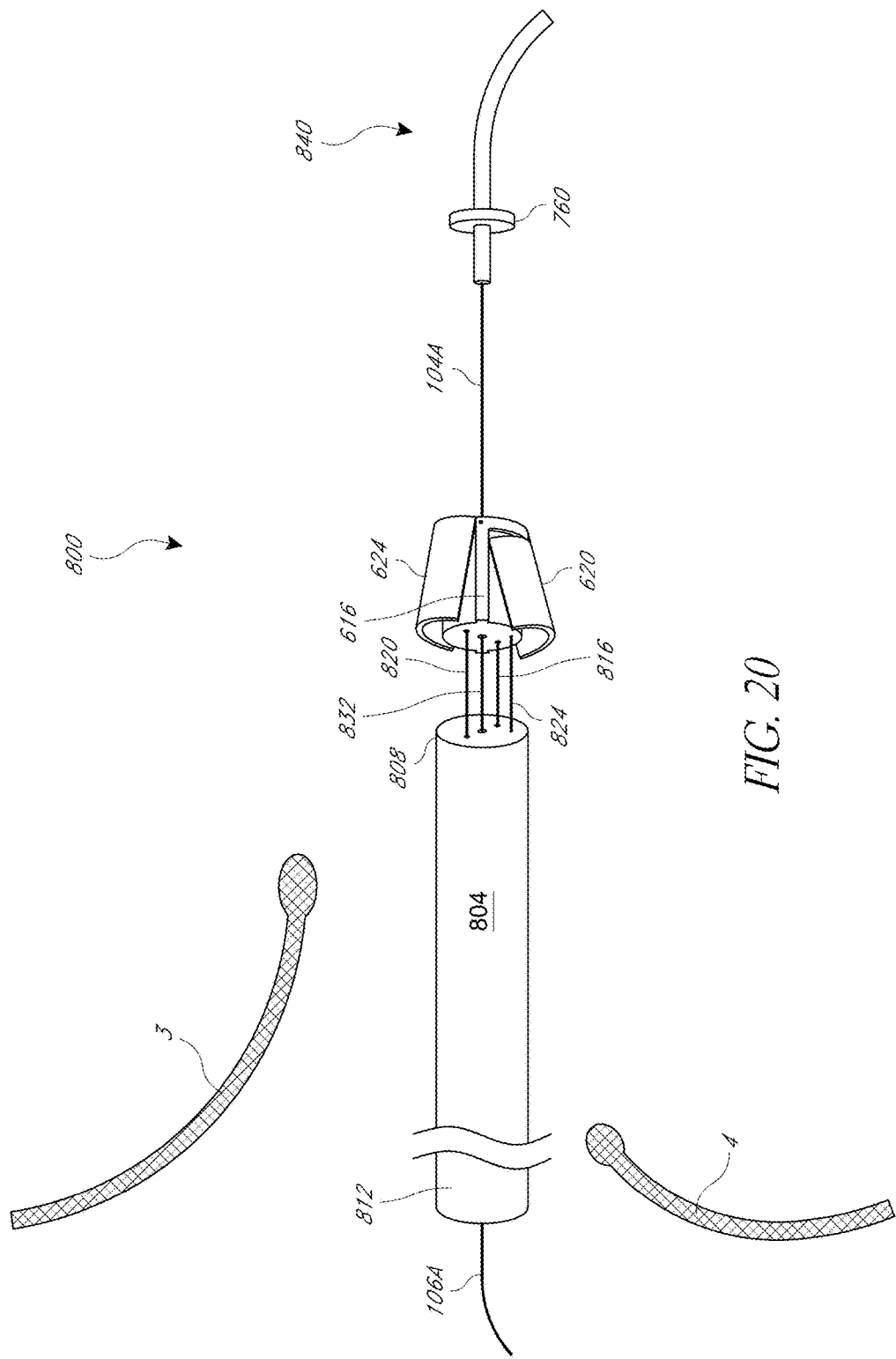
FIG. 20 illustrates part of a system for deploying the prosthesis of FIGS. 16-19.

FIG. 20 illustrates that the prosthesis 600, which may be a metallic cylindrical clip device, can be disposed on a catheter system 800. The catheter system 800 in includes a proximal or venous segment 804 that has a distal tip 808 and a proximal end 812. For simplicity, all of the anatomy is omitted except the anterior and posterior leaflets 3, 4. In certain embodiments, a control rail formed by the segments 104A, 106A is present and controls the trajectory (e.g., position and orientation) of the venous segment 804. Accordingly, the venous segment 804 can be advanced from the venous vasculature and controlled from the venous access site. In other embodiments, the catheter system 800 includes a distal segment coupled with a distal face of the prosthesis 600. The distal segment, if provided, controls of the position and deployment of the prosthesis 600 from arterial access site. Thus various embodiments of the catheter system 800 control deployment of the prosthesis 600 from one or both of a venous access site and an arterial access site. The proximal end 812 of the proximal segment 804 is disposed outside the patient, e.g., exiting a femoral vein or other peripheral vascular segment. The body of the proximal segment 804 is long enough to reach from the peripheral venous site at least to the mitral valve but in certain embodiments through the heart into the arterial vasculature as discussed above. One or a plurality of control elements extend though of a catheter system 800. FIG. 20 shows that one embodiment provides a fluid delivery channel 816 to deliver control fluid to the actuator 704 in driving engagement with the posterior element 620. A fluid delivery channel 820 is provided to deliver control fluid to the lumen 732 and to an actuator disposed in fluid communication with the lumen 732. Control fluid delivered through the fluid delivery channel 820 acts on the actuator to actuate the anterior element 624.

An indexing member 824 can be selectively engaged with the indexing feature 744 to orient the prosthesis 600 about the longitudinal axis there of or relative to the proximal segment 804 or the leaflets 3, 4. The indexing member can be an elongate slender rod or any of the other features discussed hereinabove or another suitable structure.

A push element 832 can be engaged with the threaded recess 740. The push element 832 can extend to the proximal end 812 and to an actuator device to be manipulated by the clinician. In one embodiment, the push element 832 has a lumen that enables the proximal segment to be delivered over a guidewire or rail.

FIG. 20 shows an example of delivery over a rail. In particular, a rail including proximal and distal segments 106A, 104A is established by any of the techniques discussed above. The prosthesis 600 disposed at the end of proximal segment 804 of the catheter system 800 is then advanced over this guidance rail from the venous access site. In other words, in this method, the combination of the proximal and distal segments 106A, 104A form a guide rail and the prosthesis 600 is disposed within a separate catheter that is guided over this rail to the heart. If advanced from the venous side, the catheter system 800 is advanced into the right atrium, across the atrial septum, into the left atrium, and to the mitral valve over the rail formed by the proximal and distal segments 106A, 104A.

The anterior element 620 is posited to face the anterior leaflet 3. Utilizing fluid pressure in the fluid delivery channel 816, the anterior element 620 facing the anterior mitral leaflet 3 is opened and held in the open position. By advancing and withdrawing the catheter carrying the prosthesis 600 along the guidance rail (combination of segments 104A, 106A), the posterior leaflet 4 is directed between the surface 620A of the anterior element 620 and the surface 672 of the base 616, at which point fluid pressure to the anterior element 620 is removed. This allows the anterior element 620 to return to the closed position. Then, utilizing fluid pressure in the fluid deliver channel 820, the anterior element 624 facing the anterior leaflet 3 is opened and held in the open position. The catheter carrying the prosthesis 600 over the guidance rail (104A, 106A) is then manipulated to position the anterior leaflet 3 between the surface 624A of the posterior element 624 and the surface 676 of the base 616, at which point fluid pressure is removed or decreased, allowing the posterior element 624 to return to the closed position. At this point, the anterior and posterior leaflets 3, 4 will be fastened together by the prosthesis 600, and positioned along the guidance rail. After the leaflets 3, 4 have been grasped the push element 832 can be disengaged from the threaded recess 740.

In some methods, the retention member 760 is thereafter applied to the prosthesis 600. In one approach, catheter body 840 is advanced over the guide rail from the arterial access site, e.g., over the distal segment 104A. The catheter body 840 is placed over the guidance rail and advanced toward the prosthesis 600 at the mitral valve. The catheter body 840 can be advanced to be adjacent to the prosthesis 600 and in one approach docks with the distal end 612 of the body 604 (e.g., by a threaded or other secure connection). The retention member 760 is engaged with the catheter body 840. In FIG. 20 the retention member 760 is shown as much larger than the body 840 but would generally be disposed flush on a surface of the body 840. The surface would have an outer diameter approximately the same as or slightly larger than the diameter of the body 604 of the prosthesis 600. A sheath (not shown) or other pushing rod or member disposed over or within the catheter body 840 can be brought into engagement with a proximal face of the retention member 760 and when urged distally on the catheter body 840 can cause the retention member 760 to be urged off of the catheter body 840 onto the prosthesis 600. Thus the retention member 760 can be urged over the distal end 612 of the body 604 to a position around the grasping element 620, 624 to the position shown in FIG. 16. The retention member 760 is configured to hold both of the grasping element 620, 624 against the body 616 in the closed position and protect against inadvertent clip opening. The catheter body 840 is then withdrawn from the body. The distal end 808 of the proximal segment 804 is then detached from the prostheses 600, and withdrawn from the body. The guidance rail including the proximal and distal segments 106A, 104A can then be withdrawn from the body.

The prosthesis has many advantages. For example, the configuration of the prosthesis 600 allows independent actuation of each gripping element 620, 624. Although the prosthesis 600 can grip the leaflets 3, 4 simultaneously, this feature allow for independent and in some cases sequential capture of each leaflet 3, 4. This makes grasping the mitral valve much simpler than where multiple gripping elements simultaneously grip the leaflets. Because the prosthesis 600 is optimally placed in a beating heart, any features that simplify the procedure can greatly improve patient outcomes and hasten recovery.

Furthermore, the arcuate (e.g., semicircular) profile of the gripping members 620, 624 allows more leaflet material to be clipped or grasped between the surfaces 620A, 624A, and the surface 672, 676 respectively than if the engaging surfaces were less curved or flat. By lengthening the engagement area, the prosthesis 600 may provide valvular sufficiency without any additional devices. In certain conventional techniques, to fully treat certain patients multiple clips are required. The curved profile is one of the features of the prosthesis 600 that will enable patients with advanced disease to be treated with a single prosthesis in some embodiments.

Also, embodiments with fluid, e.g., hydraulic or pneumatic, actuation enable the prosthesis 600 to be very simple to operate. The proximal segment 804 is advanced through the valve and after the gripping element(s) 620, 624 are opened, the catheter 804 is withdrawn to a valve leaflet gripping position. After both leaflets are gripped, the threaded push element 832 engaged with the recess 740 is unthreaded from the recess 740 by hand rotation of the member. The indexing member 824 or other counter-torque device is used to prevent the prosthesis 600 from rotating within the delivery catheter. This reduces, minimizes or eliminates torque from being applied to the valve leaflets 3, 4. The control fluid can be advanced into the channel 700 with a syringe or simple pump or other flow control device. The syringe can be hand operated, providing direct tactile feedback to the clinician. Using a flow control device with direct tactile feedback is advantageous in enabling the clinician to automatically know from feel the state of the prosthesis 600. This approach is superior to robotic controllers that, while precise, prevent the clinician from directly and immediately being able to confirm the status of the device inside the patient's heart. Because the clinician has better information at the bedside, the procedure can be faster and safer.

Although the present invention has been disclosed with reference to certain specific embodiments of devices and methods, the inventors contemplate that the invention more broadly relates to methods disclosed above, such as those useful for orienting a catheter with respect to an anatomical structure, as well as performing diagnostic and/or therapeutic procedures in the heart or adjacent the heart. Accordingly, the present invention is not intended to be limited to the specific structures and steps disclosed herein, but rather by the full scope of the attached claims.

What is claimed is:

1. A method of performing a procedure in the heart, comprising:

providing a catheter having an elongate flexible body, a proximal end, a distal end, and a procedure zone, spaced proximally apart from the distal end, proximal and distal portion of the catheter being separable from the procedure zone;

advancing the catheter antegrade through the mitral valve, through the aortic valve and into the aorta, such that the procedure zone is positioned upstream from the aortic valve;

deploying an anterior element of a clip from the procedure zone;

positioning the anterior element over an anterior leaflet of a mitral valve;

deploying a posterior element of the clip from the procedure zone;

positioning the posterior element over a posterior leaflet of the mitral valve;

moving the anterior element toward the posterior element to clip together the anterior leaflet and the posterior leaflet;

separating at least one of the proximal portion and the distal portion from the clip; and separately removing the proximal and distal ends of the catheter from the patient leaving the clip implanted in the heart of the patient.

2. A method of performing a procedure in the heart as in claim 1, wherein the procedure zone comprises a fastening device configured to opening carried by the catheter.

3. A method of performing a procedure in the heart as in claim 2, wherein the fastening device is configured to capture adjacent edges of the valve to create a double orifice in the valve.

4. A method of performing a procedure in the heart as in claim 3, wherein the fastening device comprises a clip having proximal and distal portions detachably coupled to the proximal and distal portions of the catheter.

5. A method of performing a procedure in the heart as in claim 1, further comprising transluminally advancing the catheter through the intra atrial septum prior to the advancing step.

6. A method of performing a procedure in the heart as in claim 1, additionally comprising the steps of positioning a flow directed catheter through the mitral valve, through the aortic valve and into the aorta, advancing a guidewire through the flow directed catheter, and removing the flow directed catheter.

7. A method of performing a procedure in the heart as in claim 1, wherein the advancing step comprises advancing the catheter to position the procedure zone within a flow path between the mitral valve and the aortic valve.

8. A method of performing a procedure in the heart as in claim 1, wherein the procedure zone comprises an opening carried by the catheter.

9. A method of performing a procedure in the heart as in claim 1, wherein the opening comprises an opening in a side wall of the catheter.

10. A method of performing a procedure in the heart as in claim 1, wherein the catheter comprises an outer tubular wall having a central lumen, and an inner elongate flexible body extendable through the central lumen, and the procedure zone comprises an opening at a distal end of the outer tubular wall.

11. A method of performing a procedure in the heart as in claim 1, wherein the procedure comprises an atrioventricular valve repair.

12. A method of performing a procedure in the heart as in claim 1, wherein the procedure comprises grasping at least one leaflet of the mitral valve.

13. A method of performing a procedure in the heart as in claim 1, wherein the procedure comprises attaching the anterior leaflet of the mitral valve to the posterior leaflet of the mitral valve.

14. A method of orienting a first and second tissue grasper with respect to the mitral valve, comprising:

providing a catheter having an elongate, flexible body, with a proximal end, a distal end and first and second tissue graspers spaced apart from the distal end, each of the first tissue graspers, the second tissue graspers, and the distal end being connected to a hub;

transluminally advancing the distal end from the left atrium through the mitral valve and along the left ventricular outflow tract into the ascending aorta, whereby the first and second tissue graspers are adjacent a central zone of the mitral valve;

securing the first tissue grasper to a first leaflet of the mitral valve;

securing the second tissue grasper to a second leaflet of the mitral valve;

disconnecting the distal end from the hub; and drawing the distal end of the catheter out of a peripheral artery leaving the first and second tissue graspers implanted on the mitral valve.

15. A method as in claim 14, further comprising an extending step comprising advancing the first tissue grasper from a first position in which a longitudinal axis of the tissue grasper extends generally parallel with the flexible body, to a second position in which the axis is inclined with respect to the flexible body.

16. A method as in claim 14, further comprising actuating a distal interface to separate a distal portion of the catheter including the distal end from the tissue graspers.

17. A method as in claim 16, further comprising actuating a proximal interface to separate a proximal portion of the catheter including the distal end from the tissue graspers.

18. A method of repairing as in claim 14, wherein securing comprises applying suction to the leaflet.

19. A method of repairing a mitral valve, comprising:

introducing a first catheter through a venous access site, the first catheter having an elongate, flexible body, with a proximal end and a distal end;

transluminally advancing the distal end along a rail that extends from a peripheral vein to a peripheral artery;

deploying a valve repair device detachably coupled to the distal end to permanently connect leaflets at a midsection of a mitral valve while permitting medial and lateral portions of the natural leaflets to open and close;

introducing a second catheter through an arterial access site and advancing the second catheter along the rail to bring the second catheter into contact with the valve repair device; and transferring a retention member from the second catheter to the valve repair device.

20. A method of repairing as in claim 19, wherein the deploying step comprises positioning elements on atrial and ventricular sides of at least one of the anterior and posterior leaflets.

* * * * *